United States Patent
Wold et al.

(10) Patent No.: US 10,054,803 B2
(45) Date of Patent: Aug. 21, 2018

(54) FILTERS TO ENHANCE COLOR DISCRIMINATION FOR COLOR VISION DEFICIENT INDIVIDUALS

(71) Applicant: 3M INNOVATIVE PROPERTIES COMPANY, St. Paul, MN (US)

(72) Inventors: Chad R. Wold, West Lakeland, MN (US); Michael F. Weber, Shoreview, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 14/759,244

(22) PCT Filed: Jan. 8, 2014

(86) PCT No.: PCT/US2014/010630
§ 371 (c)(1),
(2) Date: Jul. 6, 2015

(87) PCT Pub. No.: WO2014/110101
PCT Pub. Date: Jul. 17, 2014

(65) Prior Publication Data
US 2016/0077361 A1    Mar. 17, 2016

Related U.S. Application Data

(60) Provisional application No. 61/751,994, filed on Jan. 14, 2013.

(51) Int. Cl.
*G02C 7/10*    (2006.01)
*A61B 3/06*    (2006.01)
(Continued)

(52) U.S. Cl.
CPC .............. *G02C 7/104* (2013.01); *A61B 3/066* (2013.01); *G02B 5/22* (2013.01); *G02B 5/285* (2013.01)

(58) Field of Classification Search
CPC . G02C 7/104; G02C 7/10; G02C 7/12; G02C 7/101; G02C 7/16; G02C 7/105;
(Continued)

(56) References Cited

U.S. PATENT DOCUMENTS 3,586,423 A    6/1971 Zeltzer
3,701,590 A    10/1972 Zeltzer
(Continued)

FOREIGN PATENT DOCUMENTS

CN    88200988    11/1988
CN    1062832     7/1992
(Continued)

OTHER PUBLICATIONS

JPO 2008-143028 Original and English machine translation.*
(Continued)

*Primary Examiner* — Thomas K Pham
*Assistant Examiner* — Sharrief Broome

(57) ABSTRACT

Certain filters have been found to enhance color discrimination for individuals with color vision deficiency (CVD), aka color-blind individuals. The filters generally include a multilayer optical film with a strong, narrow reflection band in part of the green region of the visible spectrum. The film has an average internal transmission from 420-680 nm of at least 50%, 60%, or 70%, and an average internal transmission≤10%, 5%, 2%, or 1% over a 10 nm wide range that includes 550 nm associated with a reflection band having a width (FWHM) of 60 nm or 50 nm or less. The filter may include a magenta layer disposed on a viewer side of the multilayer optical film to reduce glare, the magenta layer selectively absorbing green light. The magenta layer combined with the multilayer optical film may provide a rejection band whose width (FWHM) is 60 nm or less.

19 Claims, 17 Drawing Sheets

(51) Int. Cl.
*G02B 5/22* (2006.01)
*G02B 5/28* (2006.01)

(58) Field of Classification Search
CPC ...... G02C 2202/16; G02C 11/10; G02C 9/00;
G02C 11/12; G02C 3/003; G02C 7/02;
G02C 11/00; G02C 2200/02; G02C
2200/08; G02C 5/00; G02C 7/108; G02C
7/102
See application file for complete search history.

(56) References Cited

U.S. PATENT DOCUMENTS

| | | | |
|---|---|---|---|
| 3,877,797 A | | 4/1975 | Thornton, Jr. |
| 4,247,177 A | * | 1/1981 | Marks ............... H04N 13/0217 348/E13.007 |
| 4,300,819 A | | 11/1981 | Taylor |
| 4,786,125 A | | 11/1988 | Magarinos et al. |
| 4,826,286 A | * | 5/1989 | Thornton, Jr. ......... G02C 7/104 359/588 |
| 4,998,817 A | | 3/1991 | Zeltzer |
| 5,369,453 A | | 11/1994 | Chen et al. |
| 5,574,517 A | | 11/1996 | Pang et al. |
| 5,646,781 A | | 7/1997 | Johnson, Jr. |
| 5,774,202 A | | 6/1998 | Abraham et al. |
| 5,827,614 A | | 10/1998 | Bhalakia et al. |
| 5,882,774 A | * | 3/1999 | Jonza ................... B29C 55/023 359/577 |
| 6,089,712 A | | 7/2000 | Harris |
| 6,132,044 A | | 10/2000 | Sternbergh |
| 6,135,595 A | | 10/2000 | Takeshita et al. |
| 6,142,626 A | * | 11/2000 | Lu ........................... G02C 7/10 351/159.6 |
| 6,149,270 A | | 11/2000 | Hayashi |
| 6,157,490 A | | 12/2000 | Wheatley et al. |
| 6,328,446 B1 | | 12/2001 | Bhalakia et al. |
| 6,531,230 B1 | | 3/2003 | Weber et al. |
| 6,783,349 B2 | | 8/2004 | Neavin et al. |
| 7,106,509 B2 | | 9/2006 | Sharp |
| 7,264,356 B2 | | 9/2007 | Jones et al. |
| 7,284,856 B2 | | 10/2007 | Duha et al. |
| 7,784,938 B2 | | 8/2010 | Richards et al. |
| 7,951,233 B2 | | 5/2011 | Tsao |
| 8,131,518 B2 | | 3/2012 | Nakauchi |
| 2006/0092374 A1 | | 5/2006 | Ishak |
| 2007/0097509 A1 | * | 5/2007 | Nevitt .................. G02B 5/22 359/584 |
| 2009/0296040 A1 | * | 12/2009 | Ishibashi ............... A61F 9/022 351/44 |
| 2010/0062242 A1 | | 3/2010 | De Meyer et al. |
| 2011/0063726 A1 | | 3/2011 | Ramstad |
| 2012/0264239 A1 | * | 10/2012 | Cai ........................ G02B 5/20 438/15 |
| 2012/0287117 A1 | | 11/2012 | Weber et al. |

FOREIGN PATENT DOCUMENTS

| | | |
|---|---|---|
| CN | 1073266 | 6/1993 |
| CN | 1080406 | 1/1994 |
| CN | 1165967 | 11/1997 |
| DE | 19804703 | 10/1999 |
| JP | 2000-047145 | 2/2000 |
| JP | 2000-298249 | 10/2000 |
| JP | 2008-143028 * | 6/2008 |
| WO | 99/45424 | 9/1999 |
| WO | 01/57583 | 8/2001 |
| WO | 03/084448 | 10/2003 |
| WO | 2012/119158 | 9/2012 |

OTHER PUBLICATIONS

"Improving Color Vision with Lenses for the Colorblind", said to be posted by Daniel Fluck on Mar. 29, 2008, on http://www.colblindor.com/2008/03/29/improving-color-vision-with-lenses-for-the-color . . . , 15 pages.

International Search Report for PCT International Application No. PCT/US2014/010630 dated Apr. 24, 2014, 3 pages.

* cited by examiner

FILTERS TO ENHANCE COLOR DISCRIMINATION FOR COLOR VISION DEFICIENT INDIVIDUALS

CROSS REFERENCE TO RELATED APPLICATIONS

This application is a national stage filing under 35 U.S.C. 371 of PCT/US2014/010630, filed Jan. 8, 2014, which claims priority to U.S. Provisional Application No. 61/751, 994, filed Jan. 14, 2013, the disclosures of which are incorporated by reference in their entireties herein.

FIELD OF THE INVENTION

This invention relates generally to optical films, with particular application to such films that can be used to enhance color discrimination for color-blind individuals. The invention also relates to articles and systems incorporating such films, and methods of making and using such films.

BACKGROUND

Color vision deficiency (CVD), also commonly called color blindness, refers to a limited ability of some individuals to perceive differences between certain colors. CVD is caused by a lack or a deficiency of one or more color photoreceptors in the human eye. Such color photoreceptors are of three types: long wavelength (L), medium wavelength (M), and short wavelength (S) cones, which are sensitive to the red, green, and blue portions of the visible spectrum, respectively. Approximately 7-10% of males and 0.5-1% of females are color vision deficient to some degree. Red/green color blindness is the most common form of CVD.

BRIEF SUMMARY

We have developed filters that have been found to enhance color discrimination for individuals with CVD, i.e., for color blind individuals. The filters generally include a multilayer optical film with a strong but narrow reflection band in a portion of the green region of the visible spectrum. But in the remainder of the visible spectrum, the film preferably has a relatively high transmission, e.g., the film may have no significant visible reflection bands other than the narrow green reflection band. The film may have an average internal transmission from 420-680 nm of at least 50%, 60%, or 70%. The narrow green reflection band may have a width (FWHM) of 60 nm or 50 nm or less, or in a range from 20-40 or 20-50 nm. Associated with the narrow green reflection band is an average internal transmission for the multilayer optical film of no more than 10%, 5%, 2%, or 1% over a 10 nm wide wavelength range that includes 550 nm. (That is, one can find at least one 10 nm wide wavelength range that includes 550 nm (e.g., a range from 540 to 550 nm, or a range from 545 to 555 nm, or a range from 549 to 559 nm, or a range from 550 to 560 nm) over which the average internal transmission of the multilayer optical film is no more than 10%, 5%, 2%, or 1%, at normal incidence or another design angle of interest as discussed below.) In some cases the filter may consist essentially of only the multilayer optical film, while in other cases the filter may also include additional layers and coatings such as an absorptive magenta layer disposed on a viewer-side of the multilayer optical film to reduce glare, the absorptive magenta layer selectively absorbing green light. An absorption band of the absorptive magenta layer may have a width (FWHM) of 80 nm or less, and the absorption band in combination with the reflection band of the multilayer optical film may have a width (FWHM) of 60 nm or less. The filter may additionally or alternatively include other colored absorptive layers, such as a layer that selectively absorbs blue and red visible wavelengths, or a layer that selectively absorbs blue visible wavelengths. At a design angle of incidence, the filter may have an average internal transmission from 420-680 nm of at least 50%, 60%, or 70%, and an average internal transmission of 10% or less, 5% or less, 2% or less, or 1% or less (associated with a rejection band (e.g. a reflection band in combination with an absorption band) whose width (FWHM) is 60 nm or less, or 50 nm or less, or in a range from 20-40 or 20-50 nm) over a 10 nm wide wavelength range that includes 550 nm. The design angle of incidence is typically quite small, e.g., 15 degrees or less, or 10 degrees or less, or 5 degrees or less, or substantially 0 degrees, where 0 degrees refers to light propagating along an axis perpendicular to the plane of the filter or film. In many cases, the design angle of incidence may be substantially normal incidence (0 degree angle of incidence). The filters may be incorporated into eyewear or other articles. For example, the filters may be applied to lenses, windows, electronic displays, or light-transmissive shields. The filters are preferably compatible with high volume film manufacturing processes, such that an individual filter, which may be a small film piece cut from a larger film roll, may be manufactured at a reasonable cost.

The present application therefore discloses filters suitable for use in improving color discrimination for individuals with color vision deficiency. The filters include a multilayer optical film that has, at a design angle of incidence, an average internal transmission from 420-680 nm of at least 50%, and the multilayer optical film also has at the design angle of incidence an average internal transmission of 10% or less (associated with a reflection band having a width (FWHM) of 60 nm or less) over a 10 nm wide wavelength range that includes 550 nm. The multilayer optical film may have at the design angle of incidence an average internal transmission of 5% or less, or 2% or less, or 1% or less over the 10 nm wide wavelength range. The multilayer optical film may have at the design angle of incidence an internal transmission at 550 nm of 10% or less, or 5% or less, or 2% or less, or 1% or less. The filter may have at the design angle of incidence an average internal transmission from 420-680 nm of at least 60%, or at least 70%. The reflection band of the multilayer optical film may have a width (FWHM) of 50 nm or less, or in a range from 20 to 50 nm, or 20 to 40 nm. The width (FWHM) of the reflection band may define a short wavelength band edge and a long wavelength band edge of the reflection band, and the multilayer optical film may have an internal transmission, when averaged from 420 nm to the short wavelength band edge and from the long wavelength band edge to 680 nm, of at least 60%, or at least 75%, or at least 90%. The reflection band may be a harmonic of an infrared reflection band. In some cases, the filter may consist essentially of (only) the multilayer optical film, although even in those cases the filter may still be applied to other articles or bodies, such as eyewear. In other cases, the filter may include not only the multilayer optical film but also a colored absorptive layer, such as an absorptive magenta layer disposed on one side of the multilayer optical film, the absorptive magenta layer selectively absorbing green light.

We also disclose filters that include a multilayer optical film and an absorptive magenta layer, the multilayer optical film having a visible reflection band, and the absorptive magenta layer being disposed on one side of the multilayer optical film and having an absorption band that selectively absorbs green light. The visible reflection band at a design angle of incidence in combination with the absorption band provide a rejection band which has a width (FWHM) of 60 nm or less. A combination of the multilayer optical film and the absorptive magenta layer have an average internal transmission at the design angle of incidence of 10% or less over a 10 nm wide wavelength range that includes 550 nm. Also, the combination of the multilayer optical film and the absorptive magenta layer have a maximum (peak) reflectivity over a wavelength range from 500 to 600 nm of less than 50%, for light incident on the combination at the design angle of incidence and from a direction such that the light passes through the absorptive magenta layer before being incident on the multilayer optical film. The maximum peak reflectivity over the wavelength range from 500 to 600 nm may also be less than 40%, 30%, or 20%.

The absorption band may have a peak corresponding to maximum absorption and minimum transmission, the peak being disposed at a wavelength of at least 530 nm and no more than 560 nm. The peak of the absorption band may have an internal transmission of more than 20% but less than 80%. The combination of the multilayer optical film and the absorptive magenta layer may have an average internal transmission at the design angle of incidence of 5% or less, or 2% or less, or 1% or less, over the 10 nm wide wavelength range. The rejection band may have a width (FWHM) of 50 nm or less, or in a range from 20 to 50 or 20 to 40 nm. The combination of the multilayer optical film and the absorptive magenta layer may have an average internal transmission from 420-680 nm of at least 50%, at the design angle of incidence.

The absorptive magenta layer, when disposed on a viewer side of the multilayer optical film, can greatly reduce glare associated with the reflectivity of the multilayer optical film, while having little detrimental impact on the bandwidth of the rejection band and on the average transmission of the filter from 420-680 nm.

The filter may consist essentially of (only) the multilayer optical film and the absorptive magenta layer.

Eyewear is also disclosed that may include the disclosed filters.

We also disclose methods of improving color discrimination of individuals with color vision deficiency. Such methods may include filtering light perceived by the individual with a filter, the filter having, at a design angle of incidence, an average internal transmission from 420-680 nm of at least 50%, the filter having at the design angle of incidence an average internal transmission of 10% or less (associated with a rejection band having a width (FWHM) of 60 nm or less) over a 10 nm wide wavelength range that includes 550 nm. The filter may also have at the design angle of incidence an average internal transmission from 420-680 nm of at least 60%, and an average internal transmission of 5% or less over the 10 nm wide wavelength range.

The design angle of incidence, as used throughout this document, may be any suitable angle at which the filter or film is designed to operate. In most applications this angle will typically be quite small, e.g., no more than 15, or 10, or 5, or substantially 0 degrees (i.e. normal incidence). If the angle is nonzero, it causes a shift in the reflection band of a multilayer optical film to shorter wavelengths relative to the spectral position of the reflection band and normal incidence. For example, if a multilayer optical film made of alternating PET/coPMMA microlayers has a layer thickness profile that produces a narrow first-order reflection band centered at 550 nm at normal incidence (angle of incidence=0), the center of the reflection band for such a multilayer optical film shifts to 546 nm at an incidence angle of 10 degrees, and shifts to 542 nm at an incidence angle of 15 degrees. Consequently, if it is desired for the reflection band of a multilayer optical film to be centered at 550 nm (or another target wavelength) and the multilayer optical film will be mounted in a frame (e.g. an eyeglass frame) that is tilted relative to the user's line-of-sight at a modest angle of e.g. 10 degrees, then the multilayer optical film may be designed to have a reflection band whose center wavelength at normal incidence is a small amount greater than the target wavelength, e.g., approximately 554 nm if the target wavelength is 550 nm.

The foregoing specified values of the spectral width (FWHM) of a given filter or film may be based on the internal transmission of the given filter or film.

Related methods, systems, and articles are also discussed.

These and other aspects of the present application will be apparent from the detailed description below. In no event, however, should the above summaries be construed as limitations on the claimed subject matter, which subject matter is defined solely by the attached claims, as may be amended during prosecution.

BRIEF DESCRIPTION OF DRAWINGS

In the figures, like reference numerals designate like elements.

DETAILED DESCRIPTION OF ILLUSTRATIVE EMBODIMENTS

We have found that multilayer optical film technology can be used to construct filters that can substantially improve color discrimination for persons with CVD. The filter may be a narrow band green reflecting multilayer optical film, or such a multilayer optical film in combination with other layers and coatings such as an absorptive magenta layer, which selectively absorbs green wavelengths, and/or a layer that selectively absorbs blue wavelengths and/or blue and red wavelengths. Desirable filtering properties include a strong but narrow rejection band at or near 550 nm, and relatively high transmission at other visible wavelengths so that the filter does not have an unduly dark appearance. Although such filtering properties may theoretically be obtained solely with absorptive materials such as dyes and pigments, absorptive materials we investigated were unable by themselves to provide an optimal mix of both (a) sufficient blocking strength (sufficiently low transmission) at or near 550 nm and (b) a sufficiently narrow bandwidth. In contrast, multilayer optical films can be tailored to have strong blocking (very low transmission, with correspondingly high reflection) at a wavelength of interest, and in a narrow band. The transmissive and reflective properties of multilayer optical films are based on constructive or destructive interference of light at interfaces of (typically) tens, hundreds, or thousands of individual microlayers in one or more layer stacks. By appropriate selection of materials, processing conditions, and thicknesses for the microlayers, the transmission spectrum can be tailored to provide a strong but narrow reflection band, hence strong blocking in a narrow band, at or near 550 nm. The narrower the green blocking band is in wavelength space (while still being spectrally wide enough to improve color discrimination), the less light needs to be blocked in the red and/or blue portions of the spectrum to provide an improved color balance, or less blue absorption is needed.

Figure 1A:
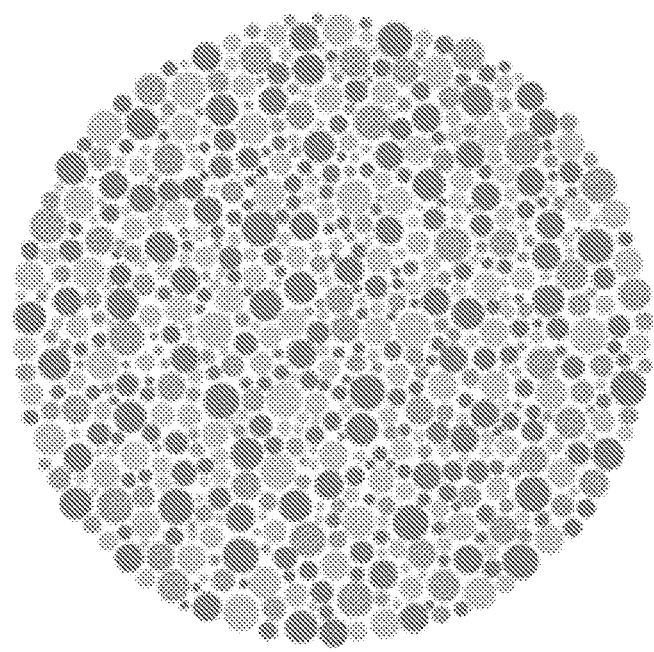
FIG. 1A is a front view of a pattern (an Ishihara color test plate or plaque) typical of those used in visual examinations to ascertain color-blindness, the pattern being in color but shown in grayscale for purposes of the figure.

One common way of testing human color perception is with a so-called Ishihara Color Test, which makes use of Ishihara color test plates or plaques. One such Ishihara test plate is shown in FIG. 1A. The individual dots that make up the pattern have different colors that form an image of a particular number. The image of the number can be perceived by individuals with normal color vision, but not by individuals with CVD. FIG. 1A is a grayscale representation of such an Ishihara test plate, and is fairly representative of the perception of an individual with CVD to the extent that no image can be discerned within the pattern of dots.

Figure 1B:
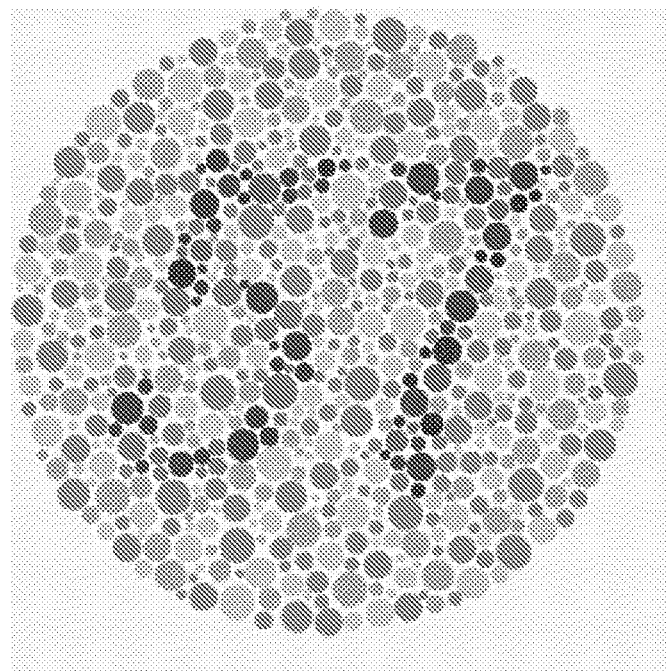
FIG. 1B is a front view of the pattern of FIG. 1 but where selected dots within the pattern have been darkened to reveal an image that would be discernible to persons with normal color vision.

FIG. 1B is a view of the same Ishihara test plate of FIG. 1A, but wherein selected dots have been darkened to reveal (in this grayscale representation) the image of the colored number. The darkened dots form the image of the number "57". This image is discernible from the Ishihara test plate to persons with normal color vision. In general, the disclosed filters allow persons with CVD to also discern the image of the number.

Figure 2:
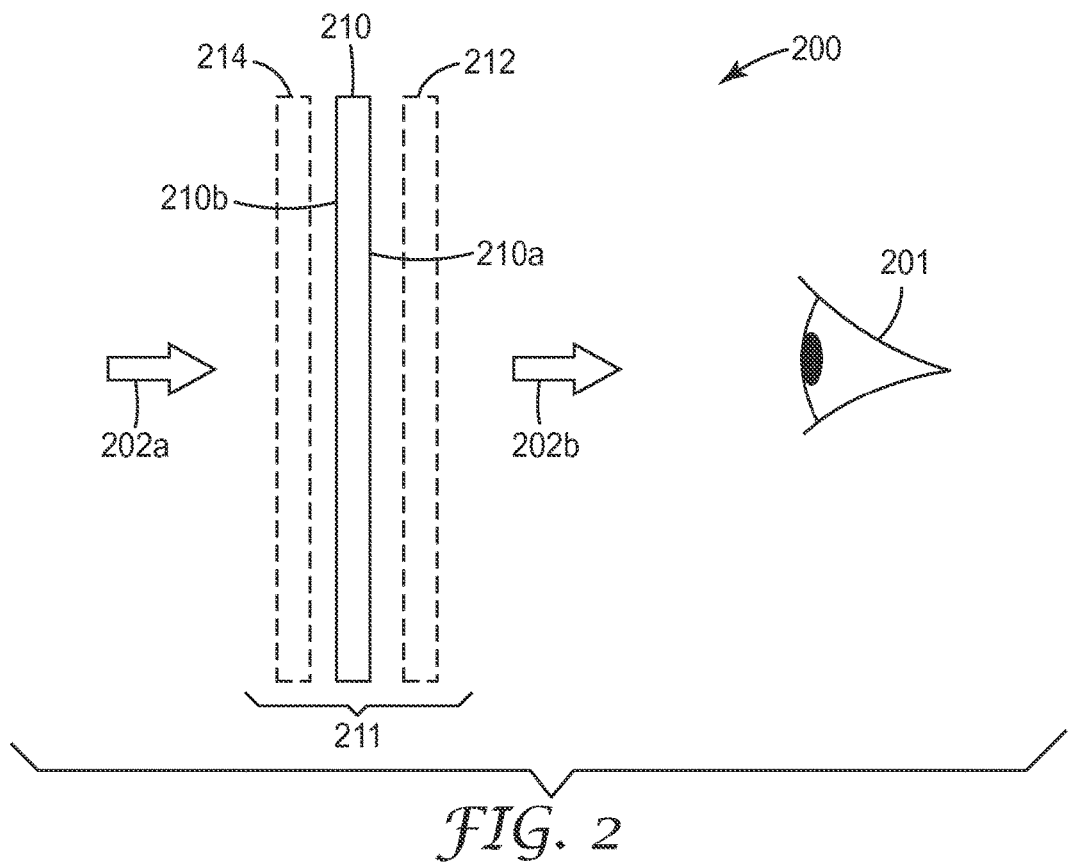
FIG. 2 is a schematic side view of a system in which a filter is used to filter light observed by a CVD individual, the filter being tailored to enhance the individual's ability to distinguish or discriminate colors.

Such a filter, used to filter light observed by a CVD individual, is shown schematically as filter 211 in the system 200 of FIG. 2. The filter 211 receives incident light 202a, and filters selected wavelengths of the light to provide filtered light 202b. The filtered light 202b is perceived by the eyes of an individual 201, which individual may have CVD. The effect of the filter 211, if designed properly, is to substantially enhance the ability of individuals with CVD to distinguish or discriminate colors. We have determined empirically that the effectiveness of the filter for this purpose can be highly dependent upon design parameters of the filter 211, such as the wavelength range of the rejection band. We have found, for example, that wavelengths at or near 550 nm are particularly effective, while wavelengths at or near 570 nm have little or no effectiveness.

The filter 211 typically includes at least a multilayer optical film 210 that has a strong but narrow rejection band at or near 550 nm, but that has relatively high transmission for other visible wavelengths. Thus, for example, the film 210 may have, at a design angle of incidence (e.g. normal incidence), an average internal transmission of at least 50% or at least 60% from 420-680 nm. The film 210 may also have at the design angle of incidence an average internal transmission of 10% or less, or 5% or less, or 2% or less, or 1% or less over a 10 nm wide wavelength range that includes 550 nm, this reduced transmission being associated with a reflection band having a width (FWHM) of 60 nm or less, or 50 nm or less, or in a range from 20 to 50 or 20 to 40 nm. These optical properties are discussed further in connection with FIG. 3. Optical properties of multilayer optical films are sometimes specified at normal incidence, or at a different incidence direction of interest, because the transmission and reflection characteristics of a multilayer optical film can substantially change as a function of the incident direction of the light.

Multilayer optical films can be designed to have a high reflectivity and low transmission for some optical wavelengths, and a low reflectivity and high transmission for other optical wavelengths. Such films ordinarily have negligible absorption, such that any light that is not reflected is substantially transmitted, and vice versa, at least over visible, near infrared, and near-ultraviolet wavelengths. Such films comprise stacks of optically thin microlayers, typically in an alternating arrangement of materials having a large refractive index mismatch, such as alternating layers of silicon dioxide and titanium dioxide, but other suitable inorganic or organic materials may also be used. Such reflectors may be made by vacuum deposition of the alternating layers on a glass or other suitable substrate, e.g., directly on the outer surface of a lens member, or on a film or substrate that can be subsequently applied to such a surface. Alternatively, suitable reflective films may be made by a continuous process that may involve coextrusion of alternating polymer materials and stretching the resulting multilayer polymer web, e.g. as described in U.S. Pat. No. 5,882,774 (Jonza et al.), U.S. Pat. No. 6,531,230 (Weber et al.), and U.S. Pat. No. 6,783,349 (Neavin et al.). Regardless of the materials used in the dichroic reflector and the method of manufacture used, the reflector is provided with a layer thickness profile for the stack of microlayers that is tailored to provide the desired transmission and reflection characteristics as a function of wavelength. The thickness profile may be tailored to provide a multilayer optical film that operates as a narrow band reflector, for example, whereby light within the narrow band of wavelengths is highly reflected (with correspondingly low transmission) and light outside of the narrow band of wavelengths is highly transmitted (with correspondingly low reflection).

The reflection band, which may also be referred to as a rejection band, of such a multilayer optical film shifts in wavelength as a function of incidence direction of the light. At normal incidence, wherein light is incident along a direction orthogonal to the plane of the film, the reflection band is at a first wavelength or range of wavelengths. Then as light is made to be incident on the film at increasingly oblique angles, the reflection band generally shifts monotonically to wavelengths shorter than the first wavelength or range of wavelengths.

In addition to film 210, the filter 211 may also include additional layers or coatings, such as an absorptive magenta layer 212 and another absorptive colored layer 214. The magenta layer 212 selectively absorbs green light and therefore has a magenta appearance in transmission. If the magenta layer 212 is applied to a major surface 210a of the film 210 that faces the observer 201, or more generally if the layer 212 is disposed between the film 210 and the observer 201, the layer 212 can advantageously be used to reduce glare caused by light reflecting from the film 210. The film 210 has particularly high reflectivity at green wavelengths associated with its narrow reflection band, thus, to maximize the reduction of glare it is advantageous for the absorption band (and/or a peak absorption) of the magenta layer 212 to be at least approximately aligned in wavelength with the reflection band of the film 210 at the design angle of incidence.

The layer 214 is another optional layer that may be included in the filter 211. In some cases, the layer 214 may be used to at least partially color correct for the film 210 and optional layer 212. That is, since the film 210 and layer 212 selectively block at least some green wavelengths and have a higher transmission for other visible wavelengths, they may tend to have a magenta color in transmission, which may be objectionable to the observer 201. To at least partially reduce the magenta color, while still maintaining the color discrimination capability of the filter 211 for CVD individuals, the layer 214 may be tailored to selectively absorb red and/or blue wavelengths. The layer 214 may be applied to a major surface 210b of layer 212 opposite the major surface 210a as shown in the figure. Alternatively, the layer 214 may be applied or disposed elsewhere within the filter 211, including between the film 210 and the layer 212, or on an outer surface of the layer 212. As mentioned above, the narrower (in wavelength) the green blocking band of the multilayer optical film is, the less red and/or blue light needs to be blocked by the layer 214 to provide an improved color balance, and vice versa.

The layer 214 (and/or other layers of the filter 211) may also be or comprise a so-called deep blue blocker. A deep blue blocker provides strong blocking (by absorption, reflection, or other mechanisms) of light in the ultraviolet range and up to approximately 400, 410, or 420 nm. Such a layer is particularly useful in the context of eyewear to protect the eyes of the user from ultraviolet and near-ultraviolet radiation.

The layers 212, 214, and film 210 are shown for illustrative purposes as being separated from each other, but typically they are attached together in a single construction, e.g. with no internal air/film interfaces. Attachment can be achieved using one or more adhesive layers, such as optically clear adhesive(s), or by other known attachment materials or mechanisms. The reader will also understand that a given component of filter 211 depicted in FIG. 2 may be replaced with two or more layers or films to accomplish the same desired function, and two or more of the components of filter 211 may be combined into a single layer or film to again accomplish the same desired function. For example, the layer 214, and/or the layer 212, may be divided into two or more layers (which may be thinner or otherwise less absorptive), which may be disposed on opposite sides of the multilayer optical film 210 if desired. In another example, dyes used to make the layers 212, 214 may be combined into a single layer that has the same transmission properties as the separate layers 212, 214. The arrangement and order of the components of the filter 211 may be rearranged as desired.

Figure 3:
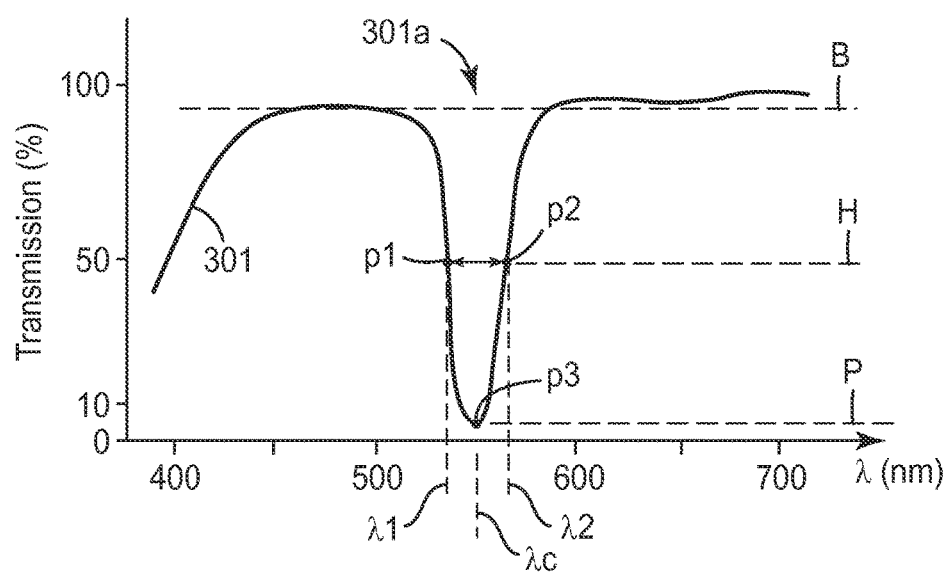
FIG. 3 is a graph of the transmission spectrum of a hypothetical filter, or a component thereof such as a multilayer optical film, the filter blocking light within a narrow band in a portion of the green region of the visible spectrum.

The transmission properties of a hypothetical filter, or of one or more components thereof such as a multilayer optical film, are shown in FIG. 3. In this figure, percent transmission is plotted against optical wavelength λ in nanometers, the wavelength axis extending over the range from 400 to 700 nm, which is sometimes treated as the human visible wavelength range. However, for purposes of this application, we consider the human visible range to be the wavelength range from 420 to 680 nm. The curve 301 may represent the measured transmission of the entire filter, or of one or more individual components thereof, at normal incidence or another design angle of incidence. Without loss of generality, for the remainder of the discussion of this FIG. 3, we will assume for simplicity that the curve 301 represents the transmission of the entire filter (note however that the filter may in some cases be only a multilayer optical film). The filter selectively blocks light within a narrow band in a portion of the green region of the visible spectrum, evidenced by the low transmission of the rejection band 301a of the curve 301. The rejection band 301a may be a reflection band, an absorption band, or the combination of a reflection band and an absorption band.

In order to quantify relevant features of the curve 301, we identify a baseline value B of the curve 301, a peak value P of the curve 301 (in this case the peak value P corresponds to a transmission minimum for the rejection band 301a, shown at point p3), and an intermediate value H of the curve 301, halfway between P and B. The curve 301 intersects with the value H at the points p1 and p2, whose wavelength values equal the short wavelength band edge λ1 and the long wavelength band edge λ2, respectively, of the rejection band 301a. The short and long wavelength band edges can be used to calculate two other parameters of interest: the width (full width at half-maximum, or FWHM) of the rejection band 301a, which equals λ2−λ1; and the center wavelength λc of the rejection band 301a, which equals (λ1+λ2)/2. Note that the center wavelength λc may be the same as or different from the peak wavelength (see point p3) of the rejection band 301a, depending on how symmetrical or asymmetrical the rejection band 301a is.

Figure 18:
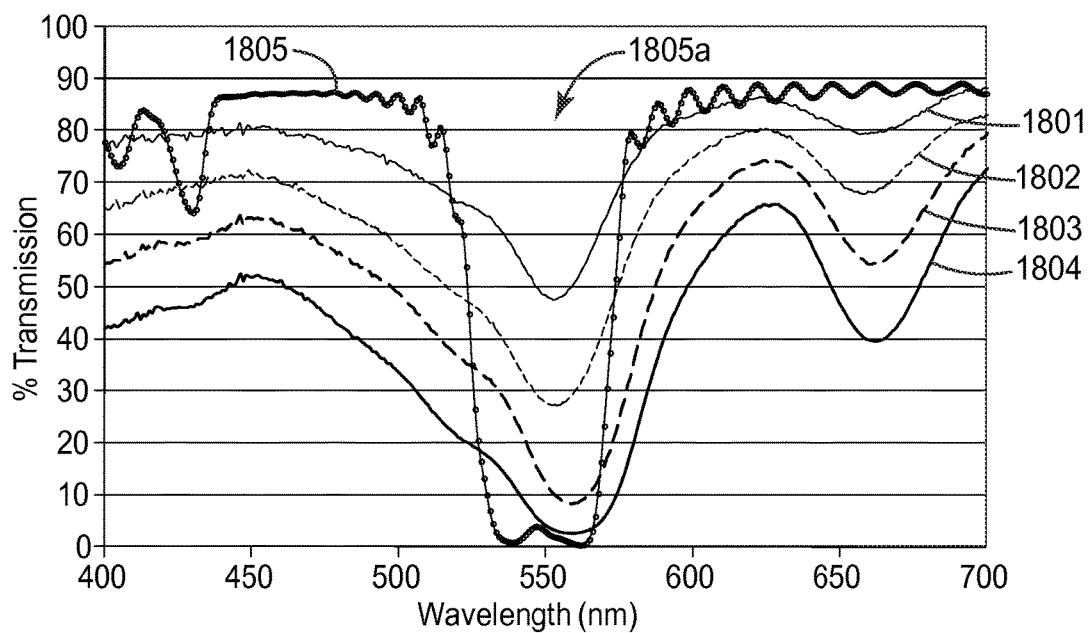
FIG. 18 is a graph of measured transmission of additional absorptive magenta layers, the graph also including the measured transmission spectrum of a narrow band green reflecting multilayer optical film.
Figure 19:
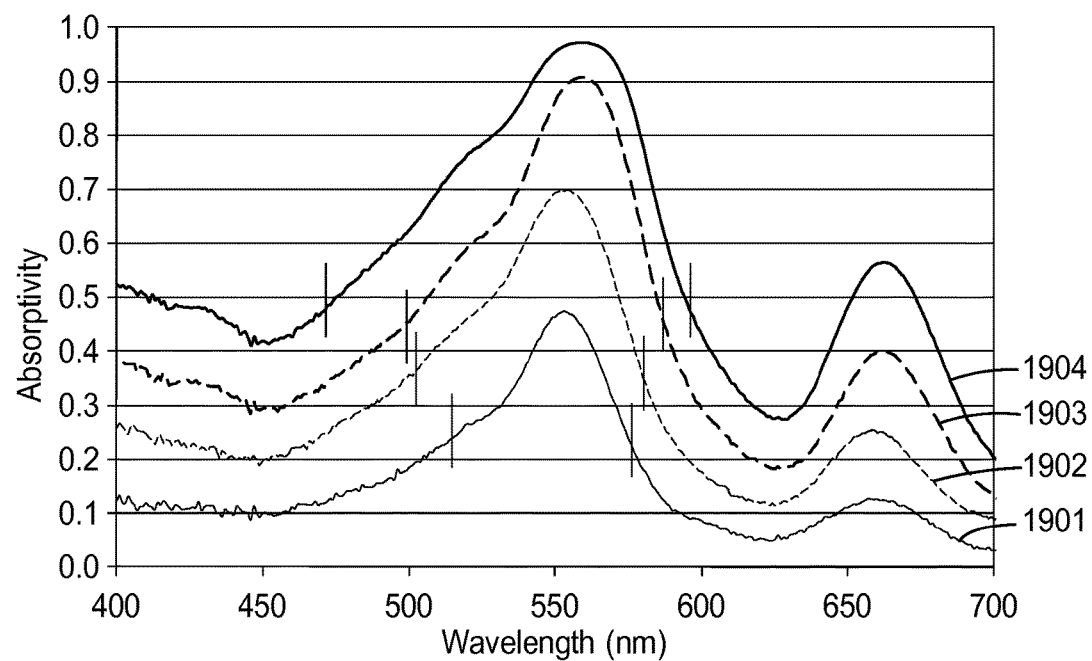
FIG. 19 is a graph of spectral absorptivity for the magenta layers in FIG. 18.

The baseline B is easy to identify for filters that have little or no absorption or reflection outside of a narrow rejection band, as illustrated by the relatively flat regions of the curve 301 on both sides of the rejection band 301a. However, in some cases a given filter may have a more complex spectrum e.g. with multiple peaks and valleys, and some filters (e.g. dyed layers) can be very broadband, exhibiting substantial absorption at all visible wavelengths, and in such cases an alternative baseline can be used. A useful baseline in these more complex filters is the 100% transmission value on a plot of the internal transmission of the filter, as defined below. Examples of such filters with more complex spectra are the absorptive magenta films whose spectra are provided below as curves 1801 to 1804 in FIG. 18. The baseline values used for calculating the spectral width (FWHM) of those dyed films was the 100% internal transmission value for the film, which corresponds to zero absorptivity in the corresponding absorptivity plots of FIG. 19.

The transmission of the filter (or component(s) thereof) refers generally to the transmitted light intensity divided by the incident light intensity (for light of a given wavelength, incident direction, etc.), but may be expressed in terms of "external transmission" or "internal transmission". The external transmission of an optical element is the transmission of the optical element when immersed in air, and without making any corrections for Fresnel reflections at the air/element interface at the front of the element or for Fresnel reflections at the element/air interface at the back of the element. The internal transmission of an optical element is the transmission of the element when the Fresnel reflections at its front and back surfaces have been removed. The removal of the front and back Fresnel reflections may be done either computationally (e.g. by subtracting an appropriate function from the external transmission spectrum), or experimentally. For many types of polymer and glass materials, the Fresnel reflections are about 4 to 5% (for normal or near-normal angles of incidence) at each of the two outer surfaces, which results in a downward shift of about 10% for the external transmission relative to the internal transmission. FIG. 3 does not specify which of these transmissions is used, hence, it may generally apply to either internal or external transmission. If transmission is referred to herein without being specified as internal or external, the reader may assume the transmission refers to external transmission, unless otherwise indicated by the context. In many eyewear lenses, the application of surface anti-reflection coatings may result in Tinternal≈Texternal.

The spectral width of a rejection band, calculated e.g. as its full width at half-maximum (FWHM), may be slightly different depending on whether it is calculated based on the internal transmission or external transmission. The FWHM calculated based on internal transmission is typically slightly greater, e.g. by less than 5 nm, than the FWHM calculated based on external transmission. In each of the tables below that report a FWHM value, unless otherwise indicated, the FWHM is calculated based on internal transmission.

Another potentially relevant feature of the curve 301 is its average (internal or external) transmission over the wavelength range from 420 to 680 nm. This parameter, which may be obtained by calculating the area under the curve 301 from 420 to 680 nm, e.g. by integration, and dividing the result by 260 nm, provides an indication of how much total visible light is blocked by the filter. The parameter may alternatively be calculated by simply averaging the (internal or external) transmission for all wavelength values (e.g. in increments of 1 nm or another suitably small increment) from 420 to 680 nm.

Another potentially relevant feature of the curve 301 is its average (internal or external) transmission over a 10 nm wide wavelength range that includes 550 nm. For example, one may calculate the average (internal or external) transmission of the curve 301 over a wavelength range from 540 to 550 nm, or a range from 545 to 555 nm, or a range from 549 to 559 nm, or a range from 550 to 560 nm.

Still another potentially relevant feature of the curve 301 is its average (internal or external) transmission over the visible region but outside of the rejection band 301a, which may be obtained by calculating the area under the curve 301 from 420 nm to λ1 and from λ2 to 680 nm, and dividing the result by ((λ1−420)+(680−λ2)) nm. This parameter may alternatively be calculated by a simple average over the portions of the visible spectrum on both sides of the rejection band.

Several types of filters were made and tested on one or more CVD individuals to determine their usefulness in helping the CVD individual(s) better distinguish or discriminate colors. These filters, some of which consisted of only a multilayer optical film, will now be described.

Multilayer optical films having a narrow reflection band can be made by co-extruding polymer resin layers so as to form relatively narrow reflection bands. The use of highly birefringent materials such as a polyester, in combination with a low refractive index material such as an acrylic, provide for large refractive index differences between alternating layers which then provide for high reflectivity in the reflection band. Several options exist for making these reflectors. In some cases, the layer thickness profile of the microlayers can be tailored to provide a first-order reflection band (at normal incidence) at a desired visible wavelength, e.g., a wavelength at or near 550 nm. In other cases, the microlayers can be made thicker such that the first-order reflection band at normal incidence is at an infrared wavelength, but a high order harmonic (e.g., a $2^{nd}$, $3^{rd}$, or $4^{th}$ order harmonic) of the infrared band is at the desired visible wavelength. This latter design approach, and subsequent polymer processing techniques, are discussed in U.S. Pat. No. 6,531,230 (Weber et al.).

For one multilayer optical film, alternating layers of polyethylene naphthalate (PEN) and polymethyl methacrylate (PMMA) were co-extruded and biaxially oriented to form a film having approximately 412 microlayers. A first group and a second group of polymeric microlayers having 275 layers and 137 layers respectively provided the film with two distinct first-order infrared reflection bands at normal incidence: a first such IR band at about 1125 nm, and a second such IR band at about 1650 nm. The $2^{nd}$ order harmonic of the first IR band substantially overlapped with, or was superimposed on, the $3^{rd}$ order harmonic of the second IR band, to yield a strong but somewhat narrow reflection band at visible wavelengths from roughly 560 to 590 nm. The measured external transmission of this film at normal incidence, in the range from 400 to 700 nm, is shown as curve 401 in FIG. 4. The visible light reflection band 401a, which is a combination of the $2^{nd}$ order harmonic of the first IR band and the $3^{rd}$ order harmonic of the second IR band, can be readily identified in the figure. (If desired, a multilayer optical film of alternative design can be made to have a similar visible light reflection band as that of FIG. 4, e.g. by providing only one first-order IR reflection band, and tailoring it so that the $2^{nd}$ or $3^{rd}$ harmonic provides a visible light reflection band similar to band 401a. Such an alternative film may have, for example, approximately 300 total microlayers, which may alternately be made of PEN and PMMA, or polyethylene terephthalate (PET) and co-polymethyl methacrylate (coPMMA), or other suitable polymer combinations. Yet another alternative multilayer optical film may provide a thickness gradient for the microlayers that produces a first-order reflection band in the visible region, similar to reflection band 401a.)

Figure 4:
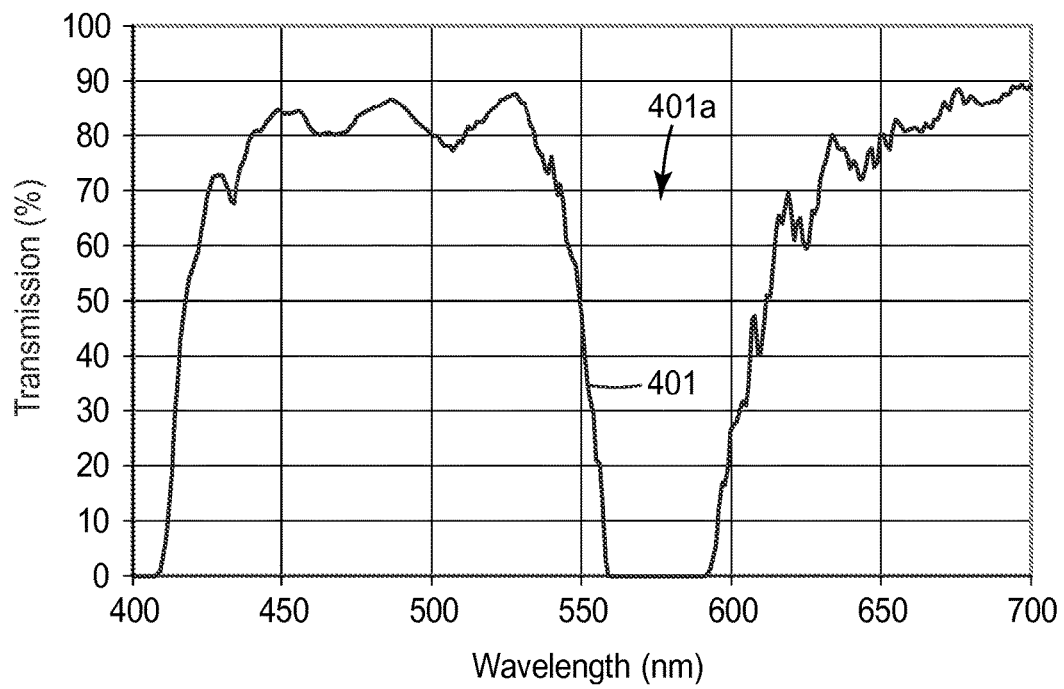
FIGS. 4 and 5 are graphs of the measured external transmission spectra of various multilayer optical films that were fabricated and tested.

The spectrum of FIG. 4 also exhibits a deep blue blocking band for wavelengths at 420 nm and lower. This reflection band is the $3^{rd}$ order harmonic of the first order IR reflection band at 1125 nm. The second order harmonic is located at 575 nm as described above. By thus utilizing various higher order harmonic bands, a deep blue blocking band can be formed using the same layers that create a desired yellow or green reflection band. For example, if a third order harmonic of an IR band is centered near 550 nm, the $4^{th}$ order harmonic band will be located near 420 nm, where the exact location will depend on the refractive index dispersion of the constituent materials used for the microlayers in the multilayer optical film.

Pertinent optical characteristics of the multilayer optical film of FIG. 4, such as the short and long wavelength band edges (λ1 and λ2) of the reflection band 401a, and other parameters, are provided below in Table 1. This film was tested by 2 CVD individuals by holding the film close to their eyes and observing Ishihara test plates and/or other colored objects through the film. The environment for these tests was an office that was illuminated with a balanced mix of diffuse sunlight and fluorescent ceiling lights. For each individual, when the plane of the film was perpendicular to the individual's line-of-sight, little or no improvement in color discrimination was experienced. However, by tilting the film at an oblique angle relative to the line-of-sight (whereupon the reflection band 401a shifted to shorter wavelengths relative to FIG. 4), the individuals each noted significant improvements in color discrimination.

Figure 5:
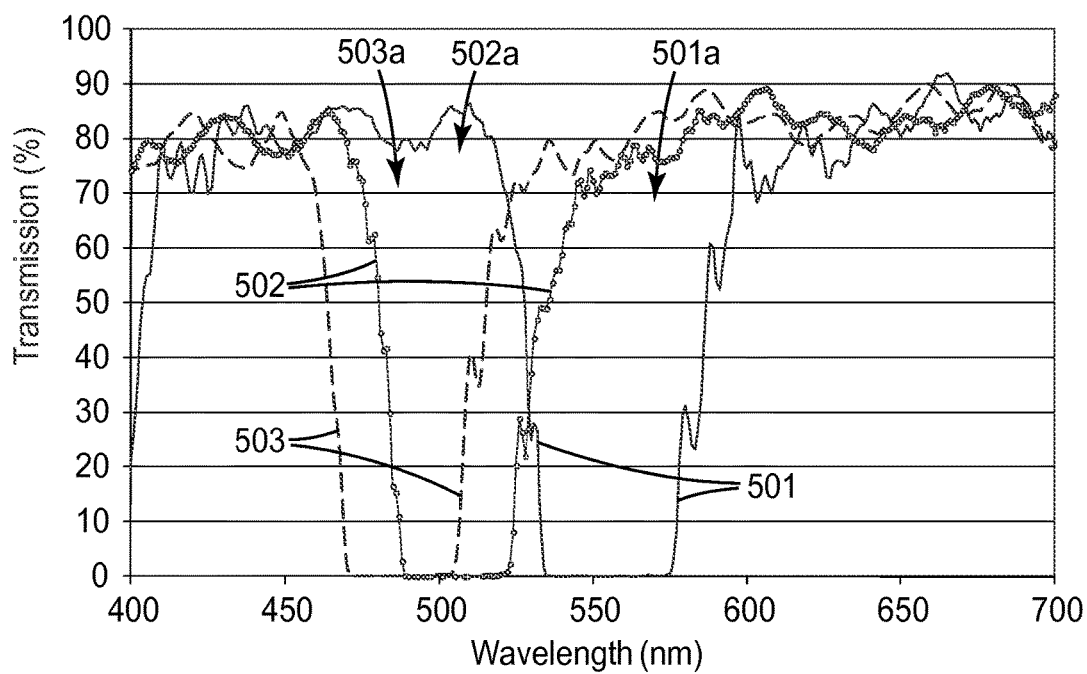

Two additional multilayer optical films were obtained by taking pieces of the film of FIG. 4 and biaxially stretching such pieces by different amounts, to yield films having the same basic construction as that of FIG. 4 (e.g., each film still had 412 total microlayers and two distinct IR reflection bands, the $3^{rd}$ and $2^{nd}$ harmonics of which again overlapped to produce one visible light reflection band), but which were thinner and thus had visible light reflection bands at shorter wavelengths than that of FIG. 4. The measured external transmission of these two additional films at normal incidence, in the range from 400 to 700 nm, are shown as curves 502 and 503 in FIG. 5. The visible light reflection bands 502a, 503a, respectively, of these films can be readily identified in the figure.

Pertinent optical characteristics of these two additional multilayer optical films (identified by their labels 502, 503 in FIG. 5) are provided below in Table 1. These films were tested by 2 CVD individuals by the use of eyewear frames in which the film was held close to their eyes at normal incidence with a cylindrical radius of curvature of about 60 mm and with the center of curvature of each lens positioned directly behind the retina of each eye and observing Ishihara test plates and/or other colored objects through the film. The environment for these tests was an office that was illuminated with a balanced mix of diffuse sunlight and fluorescent ceiling lights. For each individual, regardless of whether the plane of the film was perpendicular to the individual's line-of-sight or at an oblique angle, little or no improvement in color discrimination was experienced.

Another multilayer optical film was made. This film was made in similar fashion to that of FIG. 4, but the speed of the casting wheel during extrusion was modified. The film again had 412 total microlayers and two distinct IR reflection bands, the $3^{rd}$ and $2^{nd}$ harmonics of which again overlapped to produce one visible light reflection band. The visible wavelength reflection band at normal incidence was at shorter wavelengths relative to the film of FIG. 4, but at longer wavelengths relative to the films associated with curves 502, 503. The measured external transmission of the film at normal incidence, in the range from 400 to 700 nm, is shown as curve 501 in FIG. 5. The visible light reflection band 501a of this film can be readily identified in the figure.

Pertinent optical characteristics of this multilayer optical film (identified by its label 501 in FIG. 5) are provided below in Table 1. This film was tested by 2 CVD individuals by the use of eyewear frames in which the film was held close to their eyes at normal incidence with a cylindrical radius of curvature of about 60 mm and with the center of curvature of each lens positioned directly behind the retina of each eye and observing Ishihara test plates and/or other colored objects through the film. The environment for these tests was an office that was illuminated with a balanced mix of diffuse sunlight and fluorescent ceiling lights. For each individual, when the plane of the film was perpendicular to the individual's line-of-sight, significant improvement in color discrimination was experienced.

TABLE 1 optical properties of various multilayer optical films

| Film (curve label) | λ1 (nm) | λ2 (nm) | FWHM bandwidth (nm) | λ center (nm) | int T % avg 10 nm range incl. 550 nm | int T % avg 420 to 680 | int T % avg 420 to λ1, λ2 to 680 |
|---|---|---|---|---|---|---|---|
| 401 | 551 | 611 | 60 | 581 | 25.2 (550-560) | 87.8 | 70.6 |
| 501 | 528 | 586 | 58 | 557 | 0.00 (545-555) | 71.6 | 89.6 |
| 502 | 481 | 531 | 50 | 506 | 77.1 (540-550) | 74.0 | 89.3 |
| 503 | 464 | 515 | 51 | 489 | 85.9 (540-550) | 75.0 | 90.6 |

One would expect similar color enhancement results for CVD individuals from filters made from dyed or pigmented films rather than multilayer optical films, provided the dye or pigment is sufficiently strongly absorbing in a sufficiently narrow absorption band. However, most dyes do not have a particularly narrow absorption band, and a dyed film having both strong blocking (low transmission) and a band width (FWHM) of no more than approximately 60 nm or 50 nm is difficult to obtain. The narrowest bandwidth green absorbing dye that could easily be found was a dye known as Epolight™ 5391 Visible Light Dye, sold by Epolin, Inc., Newark, N.J. Five different absorptive filters were made by coating this dye in different amounts on a clear carrier film. Due to the green absorption, these filters or films each had a magenta appearance in transmission.

The Epolight 5391 dye was incorporated in a Vitel coating on a clear PET base film. Both the Vitel and the 5391 dye were dissolved in Methyl Ethyl Ketone (MEK) in different ratios, and then coated to different thickness values with Mayer rods onto a 50 micron clear polyester film. Mixing and coating details are summarized in Table 2 for a heavy dye solution and in Table 3 for a lighter dye solution. These samples were handmade coatings, thus, the uniformity was not as good as a production coating operation, and the results may vary. However, it is a simple matter to adjust either the coating thickness, or the dye concentration in the Vitel, as needed. Many other polymers could also be used as the dye carrier. Coating solutions for two concentrations of the dye in the Vitel are given in Tables 2 and 3, the latter being half the concentration of the first in terms of percent solids of dye to the total solids. With these two mixtures, a large range of optical density of dye coating can be made using different coating thickness values with various Mayer rods.

TABLE 2 heavy dye solution

| Ingredient | Amount (g) | Wt % of total | Wt % of solids |
|---|---|---|---|
| Epolight 5391 dye | 0.1 | 0.14% | 1.2% |
| MEK | 51.2 | 74% | |
| Vitel 2200 Copolyester | 8 | 12% | 98.8% |
| Toluene | 10 | 14% | |
| Total | 69.3 | 100% | |
| Coating solution | % Solids | 11.7% | |

TABLE 3 lighter dye solution

| Ingredient | Amount (g) | Wt % of total | Wt % of solids |
|---|---|---|---|
| Epolight 5391 dye | 0.1 | 0.09% | 0.6% |
| MEK | 73.2 | 67% | |
| Vitel 2200 Copolyester | 16 | 15% | 99.4% |
| Toluene | 20 | 18% | |
| Total | 109.3 | 100% | |
| Coating solution | % Solids | 14.7% | |

Five film samples of different dye loadings were made with this procedure. (The term dye "loading" in this regard is intended to encompass dye concentration and/or dye thickness.) The measured external transmission spectra of these films at normal incidence, in the range from 400 to 700 nm, are shown as curves 601, 602, 603, 604, and 605 in FIG. 6. These curves are listed in order of decreasing dye loading, i.e., the film of curve 601 has the heaviest dye loading and the film of curve 605 has the lightest dye loading. The films of curves 602 and 603 were made using the coating characteristics of Table 1; the films of curves 604 and 605 were made using the coating characteristics of Table 2; and the film of curve 601 was made by laminating two of the films of curve 602 together with an optical adhesive. The visible light absorption bands of these films are readily apparent in the figure. These curves each have a transmission minimum (see e.g. the point p for the curve 605) at a wavelength near 550 nm. As such, the dyed films selectively absorb green visible light, and consequently each of these films had a magenta appearance in transmission. Also apparent from the figure is that the width (FWHM) of the absorption band increases as the dye loading increases, which results in the blockage of most of the green portion of the visible spectrum, and some cyan light, for the two heaviest loadings, i.e., curves 601 and 602.

Pertinent optical characteristics of these dyed films (identified by their labels used in FIG. 6) are provided below in Table 4. (The calculated FWHM in the table is obtained for absorptive plots of internal transmission as shown below in FIG. 15.) These films were tested by a CVD individual by holding each film close to his eyes and observing Ishihara test plate(s) and/or other colored objects through the film. The environment for these tests was a windowed room with a balanced mix of diffuse sunlight and fluorescent ceiling lights. For this individual, little or no improvement in color discrimination was experienced for the films of curves 603, 604, and 605. For the remaining films, i.e., those of curves 601 and 602, the CVD individual experienced some improvement in color discrimination, but the films were dark, with little green light content.

TABLE 4 optical properties of various absorptive magenta films

| Film (curve label) | λ1 (nm) | λ2 (nm) | FWHM bandwidth (nm) | λ center (nm) | λ peak (nm) | int T % at λ peak | int T % avg for 10 nm range incl. 550 nm | int T % avg 420 to 680 | int T % avg 420 to λ1, λ2 to 680 |
|---|---|---|---|---|---|---|---|---|---|
| 601 | 495 | 582 | 87 | 538 | 554 | 1.53 | 1.98 | 64.2 | 87.4 |
| 602 | 500 | 580 | 80 | 540 | 554 | 3.08 | 3.82 | 67.8 | 88.9 |
| 603 | 512 | 575 | 63 | 543 | 554 | 24.6 | 25.9 | 82.3 | 91.6 |
| 604 | 520 | 572 | 52 | 546 | 554 | 40.2 | 41.6 | 86.7 | 94.9 |
| 605 | 522 | 572 | 50 | 547 | 554 | 57.9 | 59.0 | 89.4 | 94.5 |

Figure 6:
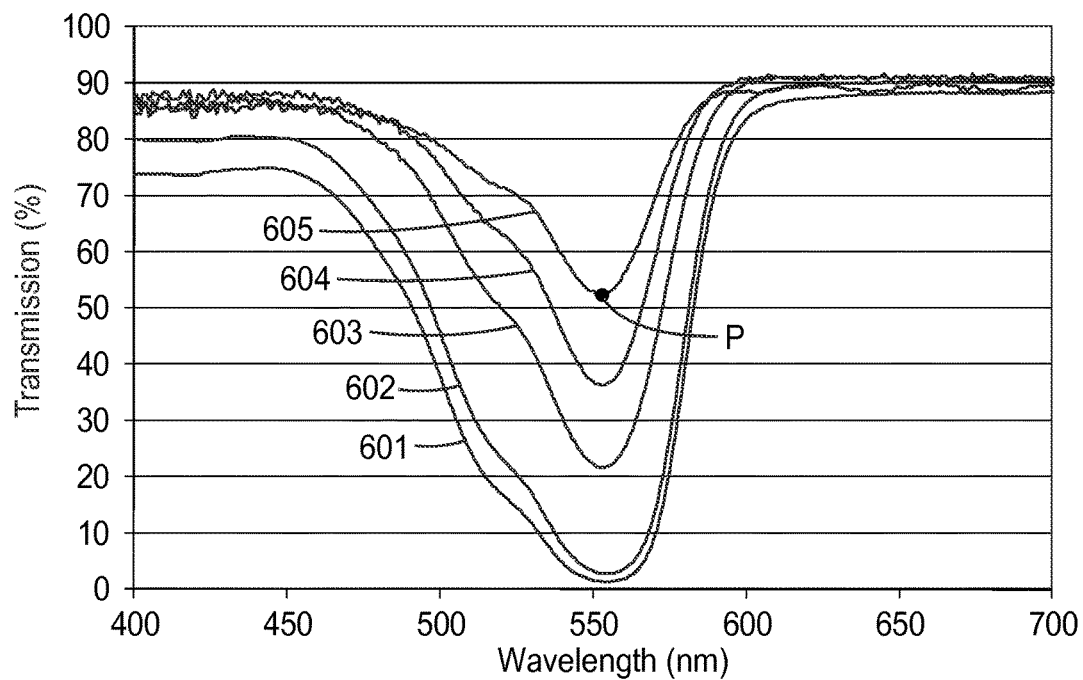
FIG. 6 is a graph of measured external transmission spectra of various absorptive magenta dyed films that were fabricated and tested.

The absorptive magenta films of FIG. 6 that have sufficient light blocking in the green region of the spectrum have bandwidths that are so wide as to produce non-optimal (dark, low light level) color viewing. However, such films that have lower dye loadings and less green light blocking can be used in combination with a narrow band green-reflecting multilayer optical film, e.g. when coated on the viewer side of the multilayer optical film, to help reduce glare from the reflector. The reflected green light that causes glare may essentially pass through the dye coating twice, allowing a lighter dye loading to provide a significant reduction in glare. This is discussed further below in connection with FIG. 12. Glare can also be reduced by design details of glasses or eyewear to which the disclosed filters are applied. For example, the eyewear may utilize a curved wrap-around design which results in less light from behind the user impinging on the lenses of the eyewear. Anti-reflection coatings, which cannot affect the reflectivity of the internal layers of the reflector, can also be added to reduce the broadband reflection of light from the surfaces of the lenses, thus further reducing glare from the lenses.

Figure 7:
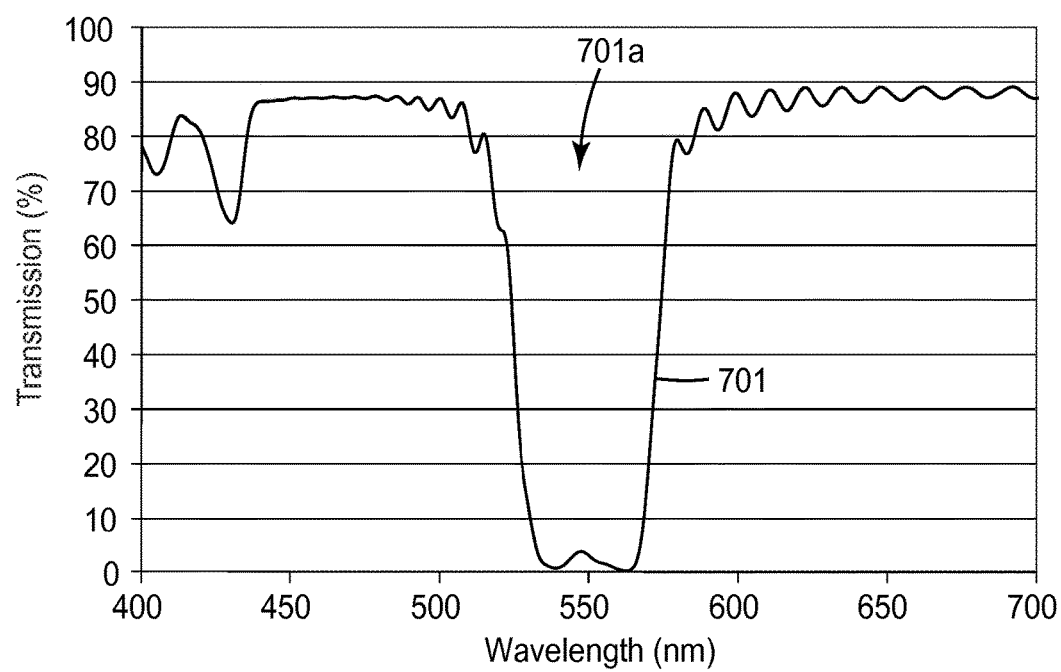
FIG. 7 is a graph of the measured external transmission spectrum of a multilayer optical film having a reflection band that blocks a portion of green visible light, the reflection band being narrower than that of the films of FIG. 5.

Further multilayer optical films were made. Like the films of FIGS. 4 and 5, these films were made by coextrusion of hundreds of alternating polymer layers, casting the multilayer extrudate onto a casting wheel, and biaxially stretching the cast film to form a multilayer optical film. In one case, a multilayer optical film was made with a stack of 223 individual microlayers, the microlayers alternating between PET and coPMMA polymer material. The layer thickness profile of the stack was tailored to produce a first-order reflection band in the infrared region of the spectrum. The $3^{rd}$ order harmonic of the IR reflection band was in the visible region at or near 550 nm. The measured external transmission of this film at normal incidence, in the range from 400 to 700 nm, is shown as curve 701 in FIG. 7. The visible light reflection band 701a of this film can be readily identified in the figure.

Pertinent optical characteristics of this multilayer optical film (identified by its label in FIG. 7) are provided below in Table 5. Note that the width (FWHM) of the reflection band 701a is less than that of reflection band 501a.

Another multilayer optical film was made with a stack of 275 individual microlayers, the microlayers alternating between PET and coPMMA polymer material. The layer thickness profile of the stack was tailored to produce a first-order reflection band in the infrared region of the spectrum. The $3^{rd}$ order harmonic of the IR reflection band was in the visible region at or near 550 nm. The optical properties of this film varied slightly as a function of position on the manufactured film web. The external transmission at normal incidence was measured at two different places on the film, and the results are shown as curves 801, 802 in FIG. 8. The visible light reflection bands 801a, 802a of this film can be readily identified in the figure.

Pertinent optical characteristics of this multilayer optical film (identified by its labels in FIG. 8 for the two measured positions) are provided below in Table 5. Note that the widths (FWHM) of the reflection bands 801a, 801b are less than that of reflection bands 501a and 701a. This film was tested by a CVD individual by the use of eyewear frames in which the film was held close to the eyes at normal incidence with a cylindrical radius of curvature of about 60 mm and with the center of curvature of each lens positioned directly behind the retina of each eye and observing Ishihara test plate(s) and/or other colored objects through the film. The environment for these tests was a windowed room with a balanced mix of diffuse sunlight and fluorescent ceiling lights. For this individual, significant improvement in color discrimination was experienced.

Another multilayer optical film was made. This multilayer optical film was a piece from another portion of the web of the multilayer optical film described above in connection with FIG. 8. The external transmission of the film was measured at normal incidence, and the results are shown as curve 901 in FIG. 9. The visible light reflection band 901a of this film can be readily identified in the figure.

Pertinent optical characteristics of this multilayer optical film (identified by its label in FIG. 9) are provided below in Table 5. Note that the width (FWHM) of the reflection band 901a is less than that of reflection bands 501a and 701a, and about the same as that of reflection bands 801a and 802a. This film was not tested separately from the films of FIG. 8.

Figure 8:
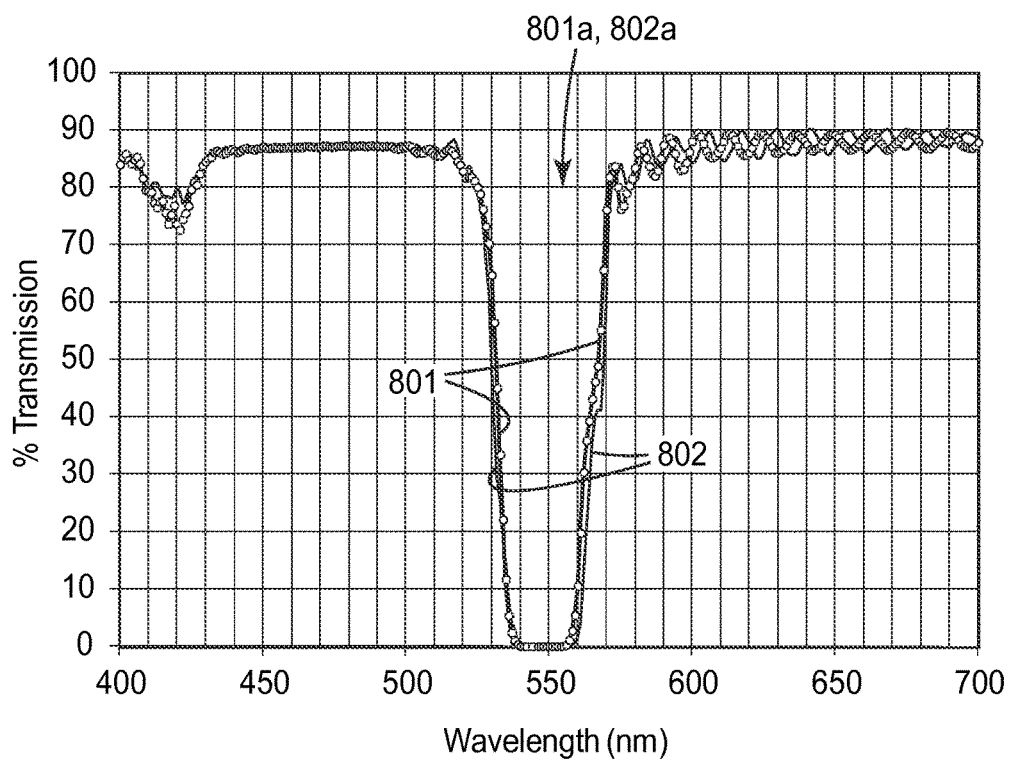
FIG. 8 is a graph of the measured external transmission spectrum of a multilayer optical film as sampled at two different places on a manufactured roll, the film samples having reflection bands that block a portion of green visible light, the reflection bands being narrower than that of FIG. 7.
Figure 9:
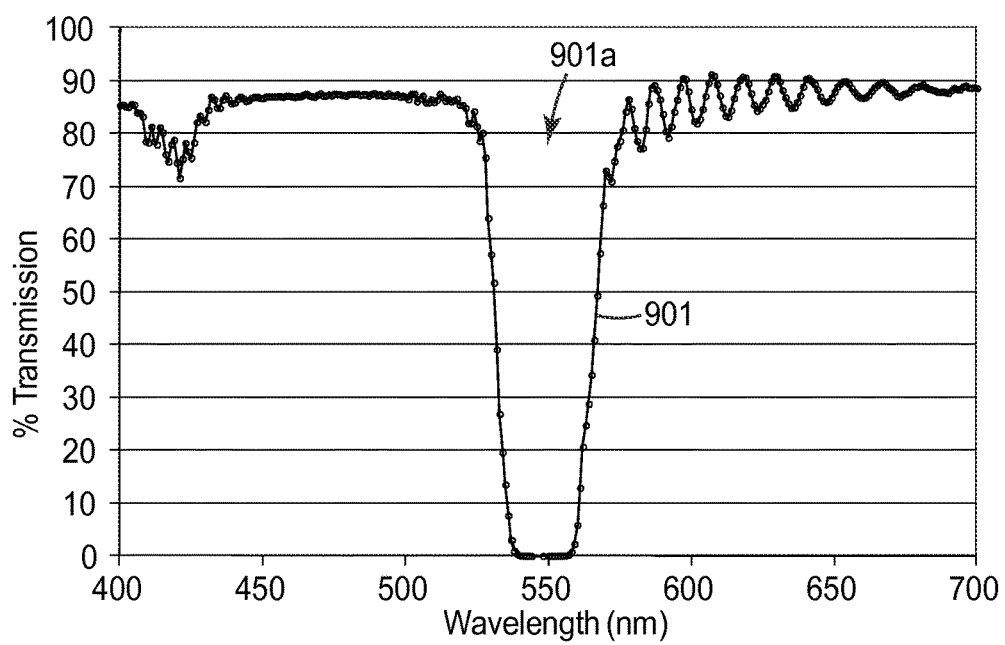
FIG. 9 is a graph of the measured external transmission spectrum of a multilayer optical film having a reflection band that blocks a portion of green visible light, the reflection band having a width similar to those of FIG. 8.
Figure 10:
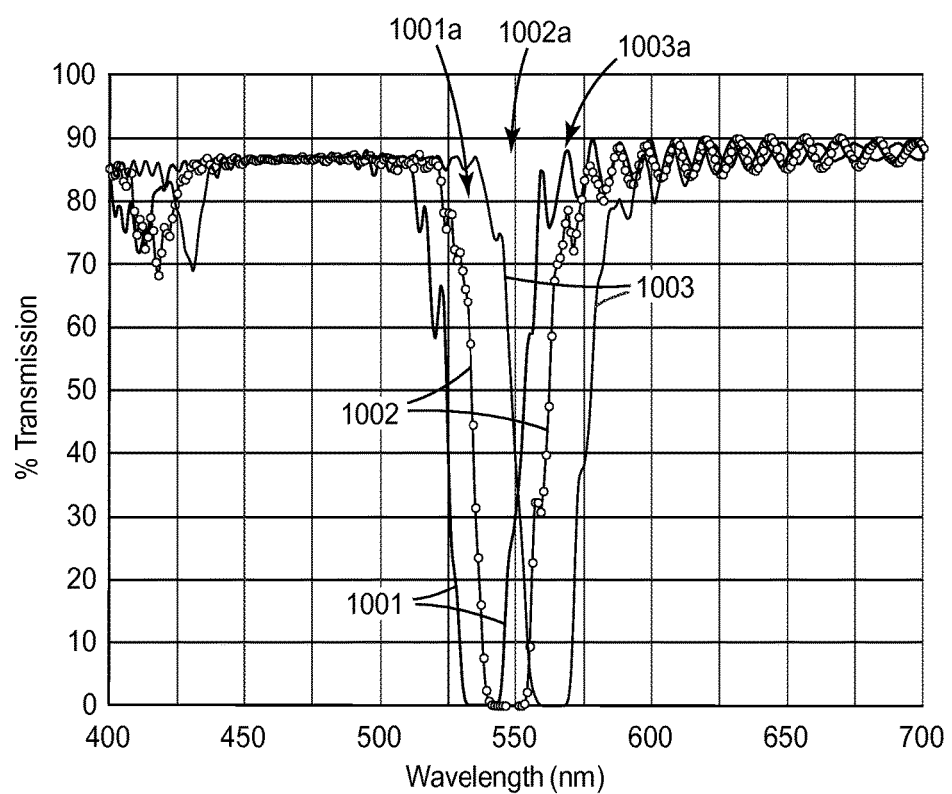
FIG. 10 is a graph of the measured external transmission spectrum of several multilayer optical films, each having a reflection band that blocks a portion of green visible light, the reflection band for each of these films being narrower than that of FIG. 9.

Still more multilayer optical films were made using the same layer count, $3^{rd}$ order reflection band, and materials as for the films of FIGS. 8 and 9, but with a slight change in the layer thickness range so as to produce an even narrower reflection band. Using the same 275 layer extrudate, three different multilayer optical films were obtained by using different casting wheel speeds. The external transmission of these films was measured at normal incidence, and the results are shown as curves 1001, 1002, and 1003 in FIG. 10. The visible light reflection bands 1001a, 1002a, 1003a of these films can be readily identified in the figure. As a result of the similar fabrication approach, the shapes of the bands 1001a, 1002a, 1003a are similar, but their band centers are shifted in wavelength due to the different stretch ratios used.

Pertinent optical characteristics of these multilayer optical films (identified by their labels in FIG. 10) are provided below in Table 5. Note that the widths (FWHM) of the reflection bands 1001a, 1002a, 1003a are less than that of reflection bands 501a, 701a, 801a, 802a, and 901a. These films were tested by a CVD individual by the use of eyewear frames in which the film was held close to the eyes at normal incidence with a cylindrical radius of curvature of about 60 mm and with the center of curvature of each lens positioned directly behind the retina of each eye and observing Ishihara test plate(s) and/or other colored objects through the film. The environment for these tests was a windowed room with a balanced mix of diffuse sunlight and fluorescent ceiling lights. For this individual, the greatest enhancement of color discrimination was experienced with the multilayer optical film of curve 1002; some enhancement of color discrimination, but a lesser amount, was experienced with the multilayer optical films of curves 1001 and 1003.

Most of the color perception tests described herein were performed indoors, with a balanced mix of diffuse sunlight and fluorescent ceiling lights, or in some cases in a room illuminated only by fluorescent lighting. We also investigated the effect of ambient lighting on the color perception tests. In particular, we investigated three different ambient lighting conditions: illumination with only fluorescent lighting; illumination with a balanced mix of diffuse sunlight and fluorescent lighting; and illumination with only sunlight. We used these different ambient lighting conditions in color perception tests for some specific multilayer optical films, each of which had a reflection band whose center wavelength was at or near 550 nm, but whose FWHM bandwidths differed. A first film was the film of curve 701, having a center wavelength of about 550 nm and a bandwidth of 48 to 49 nm, with minor variations over the area of the film. A second film was a film associated with curves 801 and 802: a different portion of the same film roll, with a center wavelength of 549 nm and with a bandwidth ranging from 35 to 38 nm due to variations over the area of the film. A third film was the film of curve 1002, having a center wavelength of 548 nm and with a bandwidth of 26 nm. Each of these three multilayer optical films was inserted into eyewear frames in which the film was held close to the eyes at normal incidence and tested by a CVD individual under the different ambient lighting conditions by observing Ishihara test plate(s) through a given one of the films, using the eyewear. The results of these tests were that, for each of the three films, substantially enhanced color discrimination was noted for the fluorescent-only illumination environment, somewhat less color discrimination enhancement was noted for the fluorescent/sunlight mix illumination environment, and less color discrimination enhancement was noted for the sunlight-only illumination environment, depending on the FWHM bandwidths. In the sunlight-only environment, the first and second films (having bandwidths of 49 nm and 37 nm respectively), particularly when they are combined with a weakly absorbing magenta dye (as described further below), helped the CVD individual to see red objects much better. The third film (having a bandwidth of 26 nm) provided little or no color discrimination enhancement in the sunlight-only illumination environment, especially when the third film was used by itself with no absorbing magenta dye.

Figure 11:
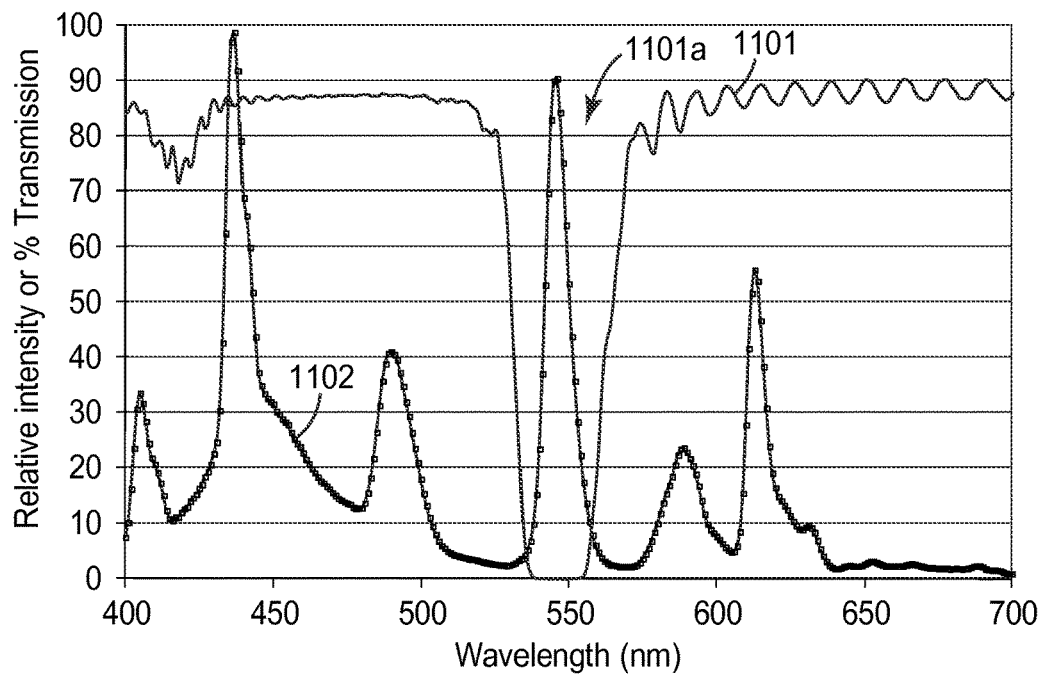
FIG. 11 is a graph of the measured transmission spectrum of a narrow band green reflecting multilayer optical film, superimposed on a graph of the relative spectral intensity of a fluorescent light source.

To provide maximum enhancement of color discrimination for CVD individuals, it is desirable for the filter (or multilayer optical film) to have a rejection band whose center wavelength ($\lambda$ center) is in a range from 540 to 560 nm at the design angle of incidence, particularly when the ambient lighting includes (partial or complete) fluorescent illumination. An alternative way of expressing this is in terms of an average internal or external transmission over the range from 545-555 nm (or over an alternative 10 nm wide wavelength range that includes 550 nm), e.g., such an average should preferably be no more than 10%, 5%, 2%, or 1%, while at the same time having few if any other visible reflection bands and a high average transmission over the visible wavelength range. FIG. 11 shows the measured transmission of a representative multilayer optical film, see curve 1101, superimposed on the measured relative intensity, see curve 1102, of a typical fluorescent office light source from some environments we used in our tests. For environments that include at least some such fluorescent light, it is presumed to be advantageous for the green reflection band 1101a of the multilayer optical film to at least partially overlap the green emission peak from the fluorescent office lights, in order to be effective for color discrimination enhancement. The curve 1101 is identical to curve 901 of FIG. 9. Therefore, pertinent optical characteristics of the multilayer optical film of curve 1101 can be found by looking up the optical characteristics for curve 901 in Table 5.

TABLE 5

| optical properties of various multilayer optical films | | | | | | |
|---|---|---|---|---|---|---|
| Film (curve label) | $\lambda 1$ (nm) | $\lambda 2$ (nm) | FWHM bandwidth (nm) | $\lambda$ center (nm) | int T % avg 10 nm wide range incl. 550 nm | int T % avg 420 to 680 | int T % avg 420 to $\lambda 1$, $\lambda 2$ to 680 |
| 701 | 524 | 573 | 49 | 548 | 3.20 (545-555) | 78.4 | 94.3 |
| 801 | 532 | 567 | 35 | 549 | 0.02 (545-555) | 85.2 | 96.4 |
| 802 | 530 | 568 | 38 | 549 | 0.02 (545-555) | 84.5 | 96.8 |
| 901 | 532 | 567 | 35 | 549 | 0.01 (545-555) | 84.6 | 96.0 |
| 1001 | 525 | 553 | 28 | 539 | 13.10 (540-550) | 86.9 | 95.5 |
| 1002 | 534 | 562 | 28 | 548 | 0.03 (541-551) | 87.0 | 95.6 |
| 1003 | 549 | 577 | 28 | 563 | 14.40 (550-560) | 86.9 | 95.3 |

Figure 12:
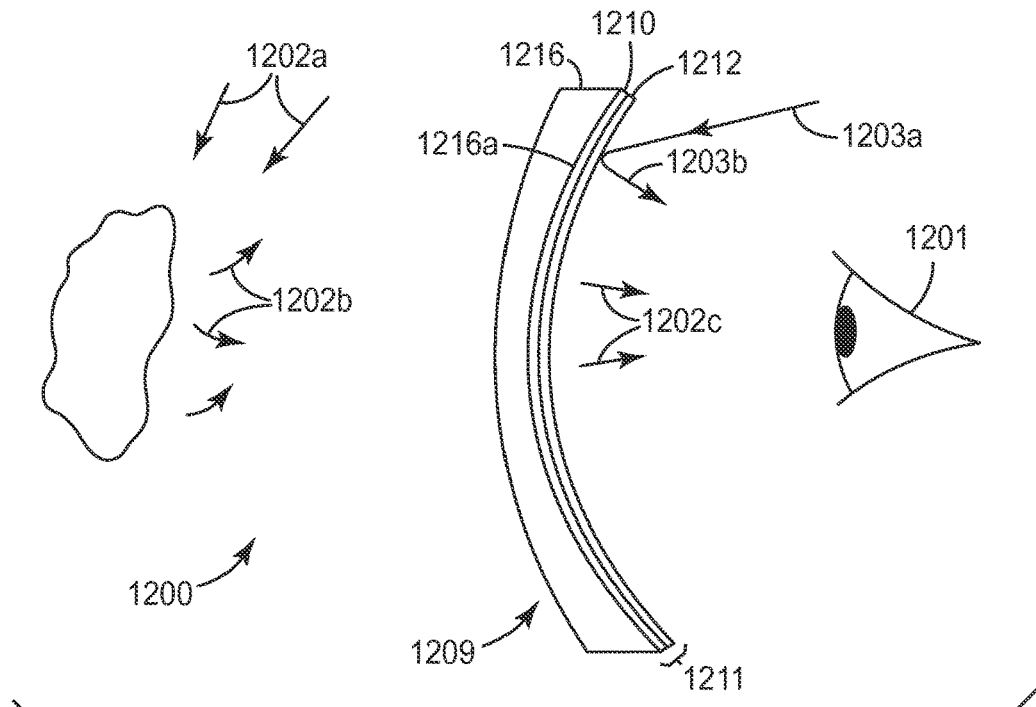
FIG. 12 is a schematic side view of a system in which a filter is applied to eyewear to filter light observed by a CVD individual, the filter being tailored to enhance the individual's color discrimination.

The system 1200 of FIG. 12 helps to illustrate the issue of glare. Ambient white light 1202a illuminates an object, which may be an Ishihara test plate or any other suitable object, and the object absorbs some light and scatters remaining light as light 1202b. An observer 1201, who may be a CVD individual, observes the object by its scattered light 1202b using eyewear 1209, e.g., goggles, spectacles, or glasses. The reader will understand that although only one eye of the observer 1201 and only one portion of the eyewear is shown, the eyewear may include another half substantially the same as that shown in FIG. 12, as well as a suitable frame, strap, and/or other support structure to hold the eyewear in place on the observer's head. The eyewear includes a lens 1216 and a filter 1211 applied to a surface 1216a of the lens. The filter 1211 may be any of the filters disclosed herein for enhancing color discrimination for CVD individuals. The lens 1216 is shown as a meniscus lens, but any other type of lens may also be used. Furthermore, the term "lens" in this context not only refers to conventional lenses that have positive or negative optical (focusing) power, but also is broad enough to encompass a flat or curved plate of uniform thickness that has zero optical power, which may function as a shield or window.

The scattered light 1202b passes through the lens 1216 and is filtered by filter 1211 to provide filtered light 1202c, which is used by the observer 1201 to perceive the object. The filter 1211 preferably includes at least a multilayer optical film 1210 and an absorptive magenta layer 1212. The multilayer optical film 1210 has a strong but narrow reflection band in part of the green region of the visible spectrum. The magenta layer 1212 selectively absorbs green light, e.g., in a relatively narrow absorption band. The filter 1211 may include other layers and features as discussed elsewhere herein, and/or it may be replaced with any of the filters described herein. The filter 1211 may be applied to the lens 1216 via an optically clear adhesive or any other suitable material or process. Preferably, attachment is such that no air gap exists between the filter 1211 and the lens 1216.

Stray light 1203a, which may originate from behind the observer 1201 or from the side of the observer 1201, or may be or comprise light reflected from the observer's face, impinges on a viewer's side of the eyewear 1209, i.e., from a direction opposite the scattered light 1202b. Such stray light may be minimized or reduced by incorporating suitable design features in the eyewear, e.g., a wrap-around design, and/or by including opaque side shields in the eyewear design. However, such design features may not be appropriate in all cases, and even when they are included, they may not eliminate enough stray light. The stray light 1203a would not typically cause a problem for ordinary eyewear, because ordinary eyewear would typically reflect only a small percentage of the stray light as reflected light 1203b, which we may also refer to as glare 1203b. But unlike ordinary eyewear, the multilayer optical film 1210 has a strong reflection band in part of the green region of the spectrum (and the reflection band shifts to shorter wavelengths at increasingly oblique angles). Therefore, even though the portion of the stray light 1203a at visible red and blue wavelengths may substantially pass through the eyewear 1209 with little reflection, at least the portion of green wavelengths within the reflection band of the multilayer optical film 1210 will be strongly reflected as glare 1203b, and such green-colored glare 1203b may be distracting, annoying, or otherwise undesirable to the observer 1201.

The absorptive magenta layer 1212 may be employed in the filter 1211 to significantly reduce such glare. To achieve this, the magenta layer 1212 is disposed on the viewer side of the multilayer optical film 1210 so that any light that becomes glare 1203b passes through the magenta layer 1212 twice. Further, the magenta layer is tailored to have an absorption band that selectively absorbs at least some green visible light, and the absorption band (and/or a peak absorption of such band) is preferably at least approximately aligned in wavelength with the reflection band of the film 1210. Since light must pass through the magenta layer 1212 twice to become glare 1203b, the magenta layer can advantageously provide a relatively large amount of glare reduction (by the mechanism of absorption) while having a relatively small peak absorption, as measured in (single pass) transmission. In exemplary embodiments: the reflection band of the multilayer optical film and the absorption band of the magenta layer combine to form a rejection band whose width (FWHM) at the design angle of incidence is 60 nm or less, or 50 nm or less, or in a range from 20 to 50 nm, or in a range from 20 to 40 nm; and/or a combination of the multilayer optical film and the magenta layer have an average internal transmission at the design angle of incidence of 10% or less, or 5% or less, or 2% or less, or 1% or less, over a 10 nm wide wavelength range that includes 550 nm; and/or the combination of the multilayer optical film and the absorptive magenta layer have a maximum percent reflectivity over a wavelength range from 500 to 600 nm of less than 50%, or less than 40%, or less than 30%, or less than 20%, for light incident on the combination at the design angle of incidence and from a direction such that the light passes through the absorptive magenta layer before being incident on the multilayer optical film; and/or an absorption peak corresponding to maximum absorption and minimum transmission of the magenta layer may be disposed at a wavelength of at least 530 nm and no more than 560 nm; and/or the absorption peak may have an internal transmission of more than 20% but less than 80%.

Figure 12A:
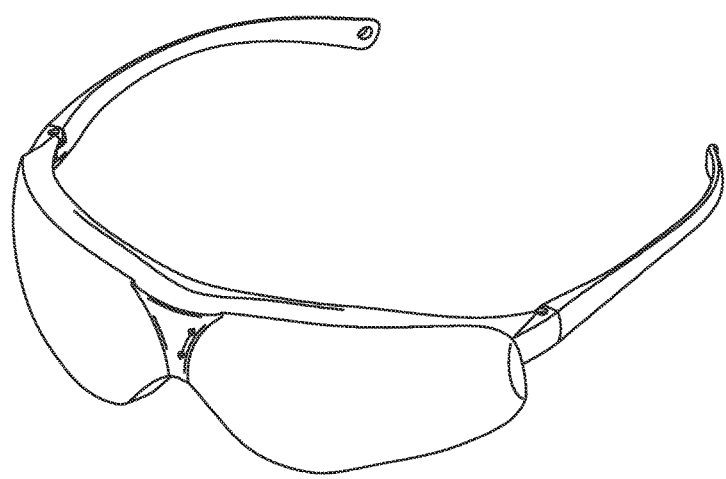
FIG. 12A is a perspective view of eyewear suitable for use with the disclosed filters.

An exemplary eyewear embodiment, including a suitable frame and pair of lenses to which the disclosed filters can be attached or otherwise incorporated, is shown in FIG. 12A; however, the eyewear 1209 may have any suitable design. For corrective lens eyewear, the eyewear 1209 may tilt the filter 1211 at an angle of approximately 10 degrees relative to the user's line-of-sight, or relative to an axis normal to the user's face. The filter 1211 may be laminated or otherwise attached to either the inner or outer face of a slightly curved eyewear lens (e.g. with a radius of curvature greater than 100 mm) Multilayer optical films that are PET-based can be cold pressed to conform to such curvatures, and held there with commonly available optical adhesives, although some application of heat may be needed to conform the film to curvatures as small as 100 mm. Application of polymeric filters to lenses whose radius of curvature is approximately 100 mm or smaller can be assisted with the use of low level heating on the order of 100 degrees C. or more. Care may be taken when thermoforming the polymeric filter to small radii of curvature surfaces in order to avoid a non-uniform stretch of the film. The film can be laminated to the front or back side of a lens, or it can be attached to the eyewear as a "clip-on" structure that utilizes mechanical and/or magnetic attachment elements. Alternatively, the film can be incorporated in a lens using methods such as those discussed in U.S. Pat. No. 5,827,614 (Bhalakia et al.) and/or U.S. Pat. No. 6,328,446 (Bhalakia et al.). Other attachment techniques include injection molding of a lens material against the filter, or making the lens in two parts and then laminating the optical filter or its multiple components to one or the other of the lens parts before optically bonding the two lens parts together. The filter need not be attached to any corrective lens, but can be self-supporting and held in place by any suitable eyewear frames, e.g., conventional eyewear frames. In some embodiments, the filter, or the filter in a stiffening laminate, can be used with frames that hold each of the two filters in place mechanically in a cylindrical configuration with a radius of curvature of 40 mm or more without thermoforming. In some cases it may be desirable to include a polarizing dye on a front surface of the eyewear lens. In some cases, the eyewear 1209 may omit the lens 1216, e.g., by holding a polymeric film filter in place using suitable frames, or otherwise holding the filter to a desired angle of incidence (tilt angle) with respect to e.g. a normal direction relative to the user's face, and a desired radius of curvature, whether flat or non-flat.

We will now proceed to describe various absorptive magenta dyes and materials that may be used in the disclosed filters, e.g. in combination with the disclosed multilayer optical films to reduce glare, and we will also describe other absorptive colored layers for use in the disclosed filters.

The spectral width of a narrow band dye—if measured in terms of the dye's optical density (discussed further below)—is typically independent of dye loading. However, the spectral width as measured from a percent internal transmission, percent absorption, or absorptivity plot increases substantially with increased dye loading. This effect has significant ramifications for the performance of a filter in which a narrow band reflective multilayer optical film is combined with a narrow band dyed layer (or similar narrow band absorptive layer), both for narrow band blockage of transmitted light, and for providing a wider band for greater absorption of reflected glare.

The dye or other absorptive material or layer may be chosen to possess a green selective absorption band whose FWHM width, as measured from internal transmission, absorption, or absorptivity, is tailored to be relatively narrow by using a dilute coating with a relatively moderate peak absorption, e.g., in a range from 40% to 80%. This allows for relatively high transmission of light that falls outside of the reflection band of the multilayer optical film. When the absorptive layer is applied to the viewer side of the multilayer optical film, the double pass of light through the absorber, before and after reflection from the multilayer optical film, increases the optical attenuation of the reflective light compared to a single pass absorption because of the effective increase in absorption bandwidth and path length. In other words, the FWHM of a moderately absorbing dye is substantially greater for double pass reflected light than for single pass transmitted light. This provides for greater attenuation of wavelengths of reflected green light that are not at the peak absorption value of the dye.

In addition to glare reduction, the narrow band width of the absorptive layer (e.g. a dilute dye) provides a similar color in transmission to the viewer as the multilayer optical film at the design angle of incidence. When a filter containing both the absorptive layer and the multilayer optical film is viewed in transmission over a large range of angles, the apparent color of the composite film exhibits less noticeable color change than if the absorptive layer were omitted from the filter, or if the absorptive layer was less color selective such as a broadband gray absorbing film. This feature reduces the possible distraction of a viewer caused by the known color change of the reflection band of multilayer optical films with angle of view (see e.g. U.S. Pat. No. 6,531,230 (Weber et al.)). For off-normal viewing angles greater than about 20 or 30 degrees, the color enhancement benefit to the viewer may be reduced due to the bandshift of the multilayer reflector, but unlike some applications such as laser protection eyewear, no danger may be imposed upon the user of the eyewear in this case. In the case of laser protection eyewear, the phenomenon of reflection band shift as a function of angle is considered highly undesirable, and for that reason a multilayer reflector in such an application is generally disposed on a highly curved substrate (e.g. lens, window, or shield), e.g., a substrate whose radius of curvature is in a range from 40 to 60 mm, with the center of curvature of the substrate and reflector being generally positioned behind or near the retina of the user's eye. In contrast, the eyewear disclosed herein, and the disclosed filters applied to such eyewear, need not have such a strong curvature, although it may if desired. For example, such eyewear (e.g. lenses) and filters may have a radius of curvature greater than 100 mm, or greater than 150 mm, these ranges being inclusive of an infinite radius of curvature, i.e., a flat lens surface or filter.

Figure 13:
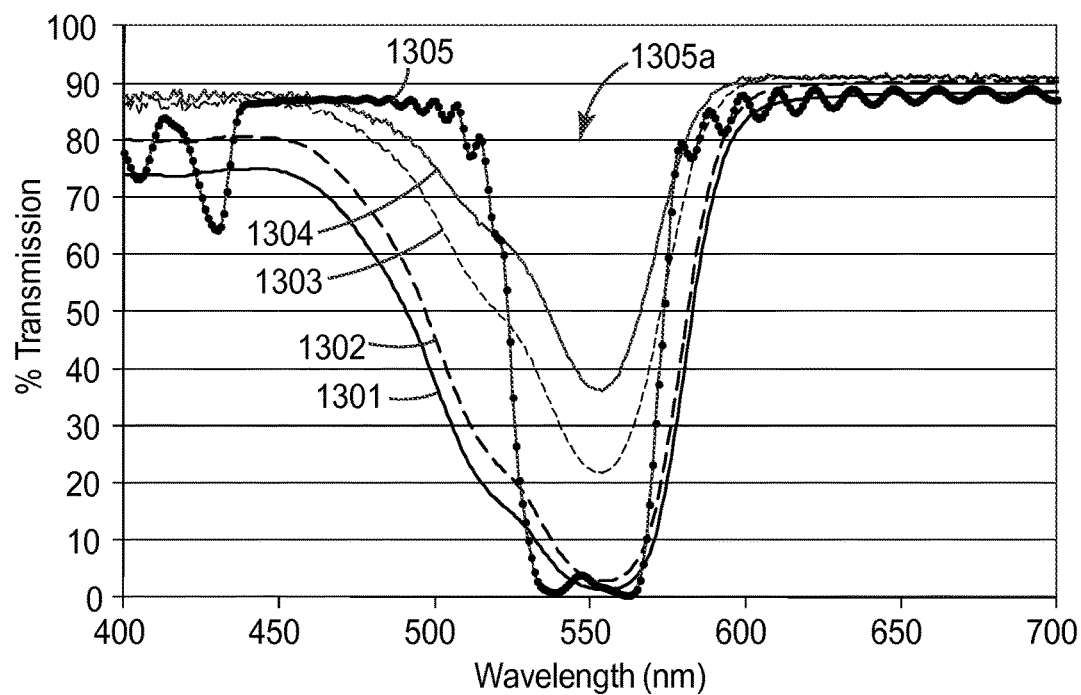
FIG. 13 is a graph that reproduces some of the measured transmission spectra of absorptive magenta films from FIG. 6, and superimposes on them the measured transmission spectrum of the narrow band green reflecting multilayer optical film from FIG. 7.

We now revisit the absorptive magenta dyed films discussed above in connection with FIG. 6, and evaluate these films in further detail. FIG. 13 reproduces the measured external transmission spectra 601, 602, 603, and 604, and simply re-labels them 1301, 1302, 1303, and 1304, respectively. The films associated with these spectra used different loading amounts of the Epolight™ 5391 dye, as described above. FIG. 13 also superimposes on these spectra the measured external transmission spectrum of the narrow band green reflecting multilayer optical film from FIG. 7 (see curve 701), which spectrum is relabeled 1305 in FIG. 13. The superimposed transmission spectra demonstrate graphically how the absorption band of the absorptive magenta layer, and/or the peak absorption of the band, can be at least approximately aligned in wavelength with the reflection band of the multilayer optical film.

Figure 15:
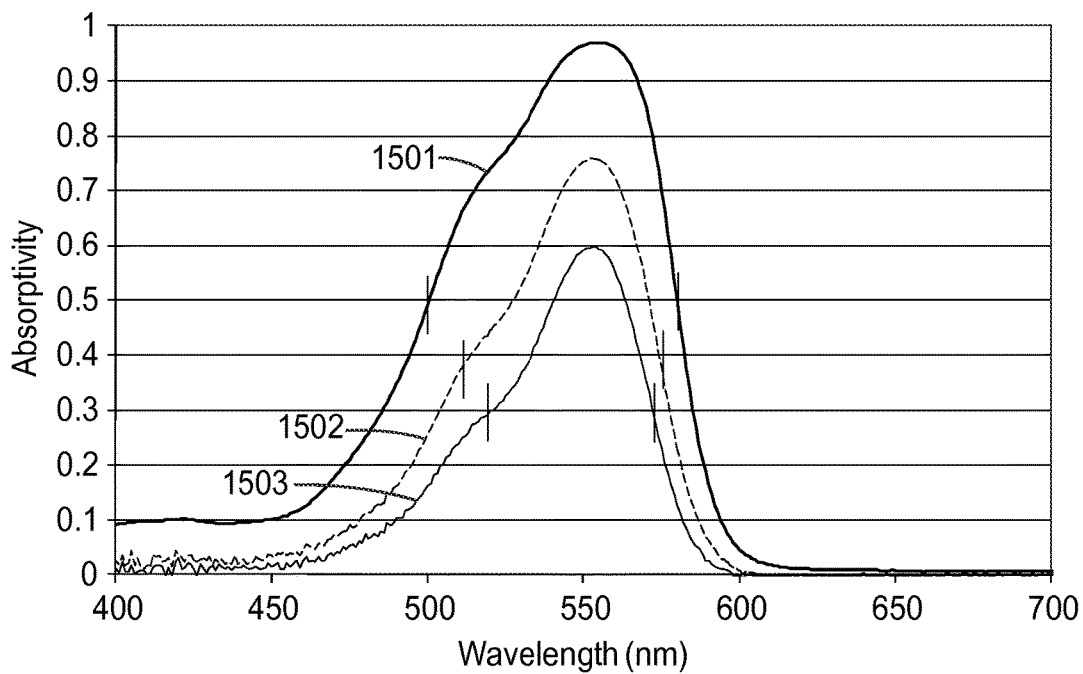
FIG. 15 is a graph of spectral absorptivity of absorptive magenta layers from FIGS. 13 and 14.

One can see both from comparison of the curves 1301-1304, and from inspection of Table 4, using data from FIG. 15 (which includes optical characteristics of the absorptive films associated with curves 1301-1304), that the FWHM width of the absorption bands of these absorptive magenta films changes as a function of dye loading. The absorption band width is narrowest for films (see e.g. curve 1304) with lesser amounts of dye loading and higher average transmission over the visible range. The absorption band width is widest for films (see e.g. curve 1301) with greater amounts of dye loading and lower average transmission over the visible. The narrower band films, with lower dye loading, can perform as acceptable narrow band glare reducers.

Interestingly, if the transmission characteristics of the absorptive magenta films is reformulated in terms of optical density (OD) or absorbance, where $$\text{optical density (or OD)} = \text{absorbance} = -\text{Log}_{10}((\text{Internal Transmission \%})/100),$$

the resulting transmission spectra of the various films exhibit absorbance widths that are much less dependent on dye loading. The optical density or absorbance of some of the dyed films of FIG. 13 was calculated by first mathematically removing the effect of the reflection of light at the polymer/air interfaces from the respective external transmission spectrum (to obtain percent internal transmission), then dividing by 100 and calculating the negative logarithm according to the equation above. The (Fresnel) reflectivity at the polymer/air interfaces can be removed mathematically with the following formula, which calculates internal transmission "Tinternal" of a film from its measured external transmission "Texternal":

$$\text{Tinternal} = (-b + \text{sqrt}(b^2 - 4ac))/2a, \text{ where:}$$

$a = r1*r2*t$ $b = 1 - r1 - r2 + r1*r2$ $c = -\text{Texternal}$ $r1$ = the reflectivity of the $1^{st}$ polymer/air surface calculated from its refractive index, and $r2$ = the reflectivity of the $2^{nd}$ polymer/air surface calculated from its refractive index.

Figure 14:
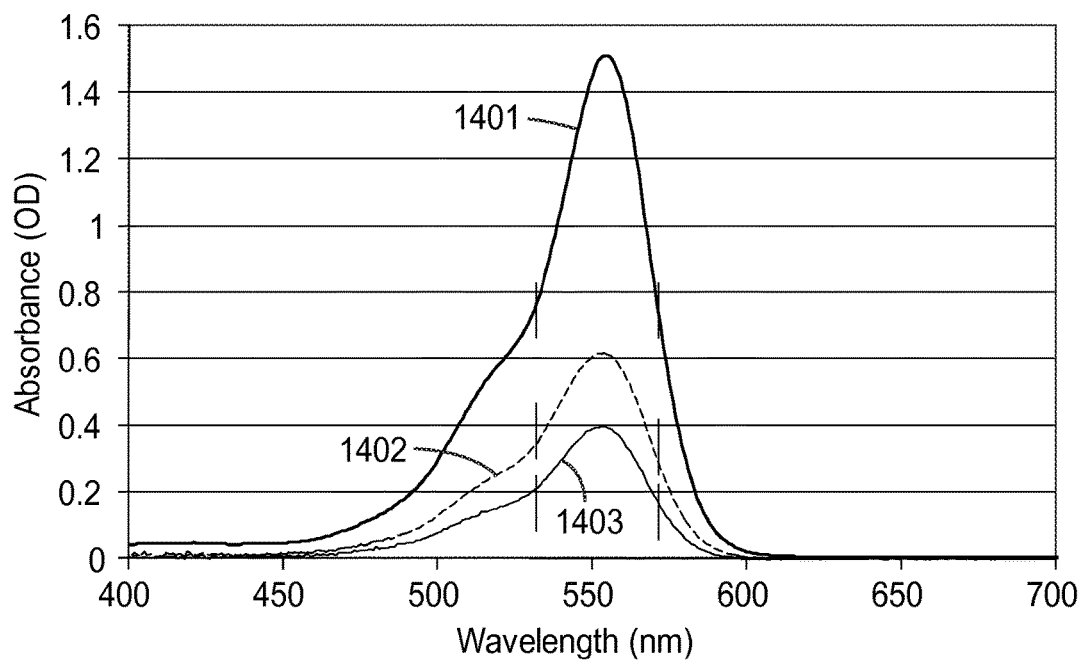
FIG. 14 is a graph of spectral absorbance (optical density) of absorptive magenta layers from FIG. 13, the absorbance being calculated from the measured transmission spectra.

The results of these calculations are shown in FIG. 14. There, curves 1401, 1402, 1403 are the calculated optical density or absorbance for the absorptive magenta films of curves 1302, 1303, and 1304 respectively. For each curve in FIG. 14, two thin vertical lines are provided to mark the short and long wavelength locations at which the absorbance is half of the maximum.

One can see from the figure that the absorbance or optical density spectra of the variously dyed films have widths (each about 40 nm) that are less dependent on dye loading. However, for the present application of color discrimination enhancement for CVD individuals, this measure of absorption bandwidth (based on optical density of the absorptive layer) is less significant than the bandwidth measured based on the fraction or percentage of light absorbed by the absorptive layer, i.e., based on the absorptivity or on the internal transmission. "Absorptivity" is a parameter that ranges between 0 and 1, and is equal to one minus the internal transmission (where the internal transmission is expressed as a decimal value rather than as a percentage). As we saw in connection with FIGS. 6 and 13, in contrast with FIG. 14, the width (FWHM) of the absorption band of the dyed films changes substantially with dye loading. However, strictly speaking, FIGS. 6 and 13 include the effects of Fresnel surface reflections, and thus are in terms of external transmission rather than internal transmission. We can easily mathematically remove the effects of the front and back Fresnel surface reflections as described above from the external transmission spectra to obtain a more rigorous result.

Following this approach, the absorptivity for the curves 1302, 1303, and 1304 was calculated and is plotted in FIG. 15 as curves 1501, 1502, and 1503 respectively. For each curve in FIG. 15, two thin vertical lines are again provided to mark the short and long wavelength locations at which the absorptivity is half of the maximum. This results in FWHM widths for the curves 1501, 1502, 1503 equal to 80 nm, 63 nm, and 52 nm, respectively. Thus, again, we see that the width of the absorption band for these absorptive magenta films increases substantially as the dye loading increases (and as peak absorptivity increases). Similarly, a double pass of light through a dye layer via reflection from an adjacent multilayer reflector effectively doubles the dye loading and thus increases the FWHM of the dye layer for reflected light compared to the FWHM of the dye layer for single pass transmitted light.

From FIG. 13 (and FIG. 15) we see that the absorptive magenta films of curves 1303 and 1304 (curves 1502 and 1503) have bandwidths that are close to the bandwidth of the multilayer optical film of curve 1305, and these two absorptive magenta films absorb a relatively minor amount of light outside of the reflection band of the multilayer optical film. Thus, in the relatively dilute coatings of these absorptive films, the bulk of the absorption occurs in a band that is already blocked by the reflection band of the multilayer optical film, and these bands (individually and together) block only a portion of the entire green visible range. A viewer who uses a filter made from the combination of the multilayer optical film of curve 1305 and the absorptive magenta layer of either curve 1303 or 1304 can therefore still perceive substantial amounts of green visible light for viewing colored objects and images, with reduced glare, while the multilayer optical film provides the bulk of the blocking capability for the selected portion of the green visible range.

Figure 16:
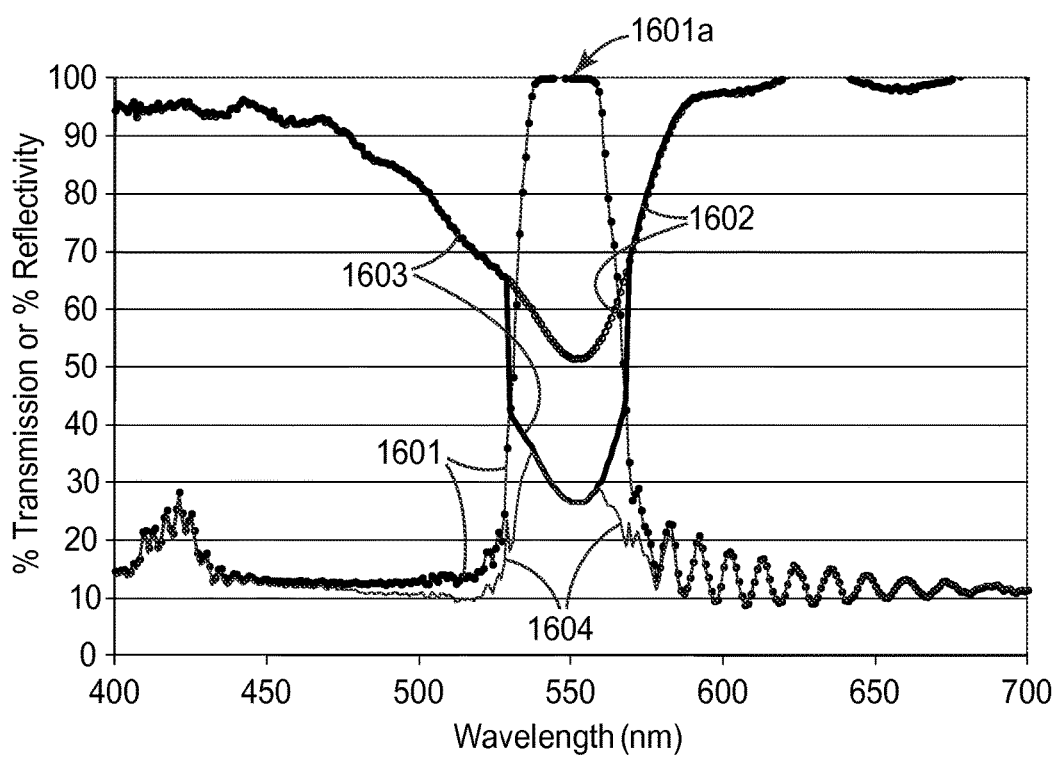
FIG. 16 is a graph that shows how glare (reflection) from a narrow band green reflecting multilayer optical film can be significantly reduced with a suitably disposed absorptive magenta layer having a moderate peak absorption.

FIG. 16 provides some exemplary transmission and reflectivity curves that demonstrate how glare (reflection) from a narrow band green reflecting multilayer optical film can be significantly reduced with a suitably disposed absorptive magenta layer having a moderate peak absorption. Curve 1601 is the reflectivity (calculated from the measured external transmission at normal incidence) of a narrow band green reflecting multilayer optical film. Curve 1602 is the internal transmission of an absorptive magenta film similar to those of FIG. 6, made using the Epolight 5391 dye. For this absorptive magenta film, the dye was dissolved in the solvents of, and then mixed with the resins of, a scratch resistant UV curable acrylate hardcoat. The acrylate was loaded with 43% silica silane and the dye loading was adjusted to give the desired peak absorption value. As shown below in Table 6, the spectral width (FWHM) of the dye in the hardcoat is greater than for the same dye in the Vitel coating. Compare the FWHM values and peak transmissions of dye curves 604 and 605 in Table 4 with that of curve 1602 in Table 6. The different dye host also shifts the peak absorption wavelength to the lower value of 551 nm from 554 nm in the Vitel. The double pass transmission of light through the magenta dye layer is approximated by curve 1603, which takes into account the fact that only light of certain wavelengths is fully reflected by the multilayer stack and undergoes the double pass through the dye layer. Curves 1603 and 1604 are calculated based on the curves 1601 and 1602. Specifically, the curve 1603 substantially tracks curve 1602, except in the region of the reflection band 1601a of the multilayer optical film. In the region of the reflection band 1601, the curve 1603 is a "double-pass" internal transmission of the absorptive magenta film, in view of the fact that light in this wavelength region passes through the absorptive magenta film twice (see FIG. 12). The peak absorption of curve 1603 is substantially greater than the peak absorption of curve 1602. By analogy with the curves of FIGS. 13 and 15 the effective FWHM of the absorption curve 1603 is also substantially greater than the FWHM of curve 1602, thus providing a wider band for greater absorption of reflected glare while providing a narrower band of absorption of transmitted light for viewing color objects and images.

The curve 1604 is the calculated overall reflectivity or glare based on the reflectivity of the multilayer optical film at normal incidence (curve 1601) and the (absorption provided by the) transmission spectrum of curve 1603. This graph takes into account the fact that not all wavelengths of light that are significantly absorbed by the absorptive magenta film are significantly reflected by the multilayer optical film, due to the limited bandwidth of the reflection band. (The effect of the shift in the reflection band as a function of incidence angle may also be considered, and is discussed below in connection with FIG. 17.) These considerations result in a complex degree of "amplification" of the width and peak absorption of the absorptive layer's absorption band.

Pertinent optical characteristics of the absorptive magenta film (identified by its label 1602) are provided below in Table 6, and pertinent optical characteristics of the multilayer optical film (identified by its label 1601) are provided below in Table 7. The reflection band of the multilayer optical film has a FWHM width that is narrower than the FWHM width of the dye. As such, the multilayer optical film will not reflect all wavelengths for which the absorptive magenta film has significant absorption, and the absorptive magenta film will not produce the full double pass absorption over its entire absorption band.

However, for light propagating near normal incidence on the film, for example due to light reflecting off the observer's eyeball or off the skin near the observer's eye, a double pass of light through the absorptive magenta film will still result in an attenuation of light that is within the bandwidth of the reflector, as shown approximately by the curve 1603 of FIG. 16. So in the case of normal incidence on a multilayer optical film with vertical band edges, the glare would still be approximately given by the curve 1604 in FIG. 16. The filter construction thus provides a substantially reduced peak reflectivity over the range from 500 to 600 nm.

Figure 17:
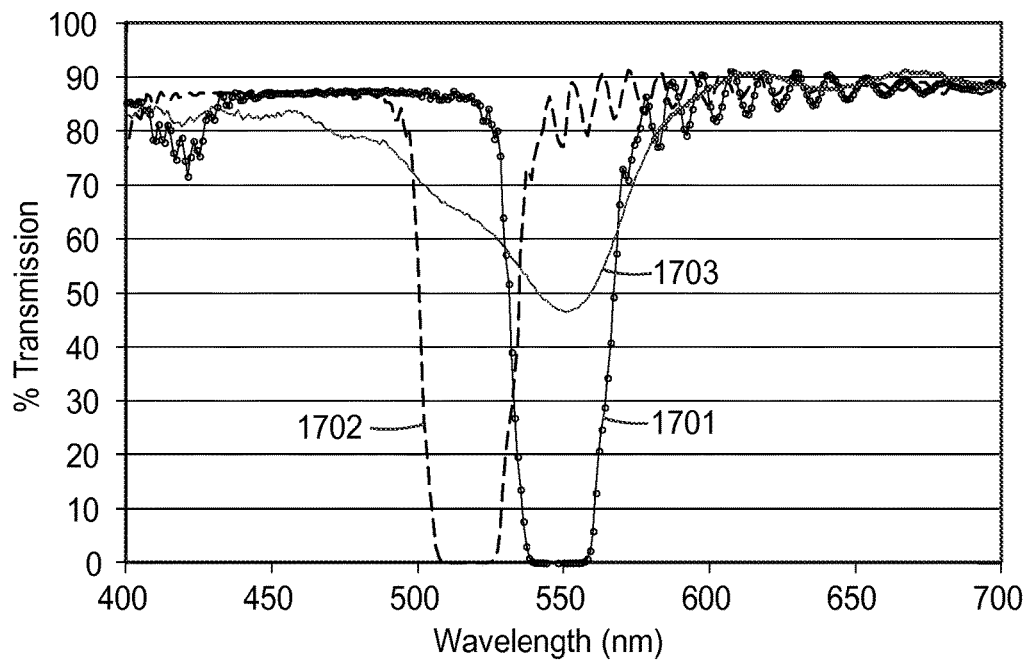
FIG. 17 is a graph of measured transmission of a narrow band green reflecting multilayer optical film at normal incidence and its calculated transmission at an oblique angle, the graph also including the measured transmission of an absorptive magenta layer.

The case of light entering the absorptive film at non-normal angles and then reflecting from the multilayer optical film (whose reflection band is spectrally shifted due to the non-normal angle of incidence) is more complex because it depends on angle. The graph of FIG. 17 investigates this situation, for the same narrow band green reflecting multilayer optical film and the same absorptive magenta film as in FIG. 16. In FIG. 17, the measured external transmission of the multilayer optical film at normal incidence is plotted as curve 1701, and the same film's calculated external transmission at an oblique angle of 30 degrees is plotted as curve 1702. FIG. 17 also includes the measured external transmission of the absorptive magenta film, labeled 1703. At the 30 degree incidence angle, the double pass of light through the absorptive magenta film occurs predominantly for wavelengths from approximately 500 to 530 nm. The absorptive film still has significant absorption at these wavelengths, and will provide some anti-glare benefits. In the example here, the use of the slightly broadened Epolight 5391 dye bandwidth in the hardcoat and its wavelength shifted peak, compared to the same dye in the Vitel, provides more absorption at the lower wavelengths. At higher incidence angles such as 45 degrees to 60 degrees, the reflectance band of the multilayer optical film will shift into the blue visible region, where the absorptive film has much less absorption, but which is also in a wavelength range that is less noticeable to the eye due to the decrease in the photopic sensitivity response of the human eye.

A broadband absorber (e.g. a broadband dye or combination of multiple dyes that collectively produce a broadband absorption) can also be used as the anti-glare layer if an anti-glare solution is desired for high intensity light reflecting from the filter at a large range of angles. Such a broadband absorber can have a relatively uniform transmission (and relatively uniform absorption) as a function of wavelength over the visible region. Although the resulting filter construction (narrowband green reflective multilayer optical film plus the broadband absorber) will have a lower total transmission of light, e.g. the average transmission of light from 420 nm to 680 nm may be less than 50%, or less than 30%, or even less than 20%, it may be useful in outdoor environments of bright sunlight where a much lower overall transmission may be desired.

TABLE 6 optical properties of various absorptive magenta films

| Film (curve label) | λ1 (nm) | λ2 (nm) | FWHM bandwidth (nm) | λ center (nm) | λ peak (nm) | int T % at λ peak | int T % avg 10 nm range incl. 550 nm | int T % avg 420 to 680 | int T % avg 420 to λ1, λ2 to 680 |
|---|---|---|---|---|---|---|---|---|---|
| 1602 | 505 | 573 | 68 | 539 | 551 | 51.6 | 52.3 | 85.5 | 93.2 |
| 1801 | 514 | 575 | 61 | 544 | 553 | 52.7 | 54.2 | 82.8 | 88.7 |
| 1802 | 499 | 580 | 81 | 539 | 554 | 30.0 | 31.3 | 68.8 | 78.6 |
| 1803 | 499 | 587 | 88 | 543 | 559 | 9.2 | 14.2 | 55.9 | 68.4 |
| 1804 | 473 | 595 | 122 | 534 | 559 | 2.8 | 4.8 | 42.2 | 57.3 |

TABLE 7 optical properties of multilayer optical film

| Film (curve label) | λ1 (nm) | λ2 (nm) | FWHM bandwidth (nm) | λ center (nm) | int T % avg 10 nm range incl. 550 nm | int T % avg 420 to 680 | int T % avg 420 to λ1, λ2 to 680 |
|---|---|---|---|---|---|---|---|
| 1601 | 532 | 567 | 35 | 549 | 0.01 (545-555) | 84.6 | 96.0 |

An alternative to the Epolight 5391 narrow band dye was investigated. The alternative was type SD-048, a narrow band dye available from Yamamoto Chemicals, Inc., Tokyo, Japan. Further absorptive magenta films were then made using the SD-048 dye in a variety of dye loadings, in a manner similar to the films made with the Epolight 5391 dye. The preparation details for four different dye loadings, some in Vitel and one in PMMA, are provided in Tables 8, 9, 10, and 11 below. Four dyed films were made by forming a hand coating of each one of these dye solutions onto a 50 micron clear polyester film using a Mayer bar #24.

TABLE 8

Vitel V2200 1:1 dye solution

| Ingredient | Amount (g) | Wt % of total | Wt % of solids |
|---|---|---|---|
| Yamamoto SD-048 dye | 0.1 | 0.17% | 1.2% |
| MEK | 42 | 70% | |
| Vitel 2200 Copolyester | 8 | 13% | 98.8% |
| Toluene | 10 | 17% | |
| Total | 60.1 | 100% | |
| Coating solution | % Solids | 13.5% | |

TABLE 9

Vitel V2200 1:2 dye solution

| Ingredient | Amount (g) | Wt % of total | Wt % of solids |
|---|---|---|---|
| Yamamoto SD-048 dye | 0.1 | 0.10% | 0.6% |
| MEK | 64 | 63.94% | |
| Vitel 2200 Copolyester | 16 | 15.98% | 99.4% |
| Toluene | 20 | 19.98% | |
| Total | 100.1 | 100% | |
| Coating solution | % Solids | 16.1% | |

TABLE 10

Vitel V2200 3:1 dye solution

| Ingredient | Amount (g) | Wt % of total | Wt % of solids |
|---|---|---|---|
| Yamamoto SD-048 dye | 0.3 | 0.30% | 3.6% |
| MEK | 82 | 81.75% | |
| Vitel 2200 Copolyester | 8 | 7.98% | 96.4% |
| Toluene | 10 | 9.97% | |
| Total | 100.3 | 100% | |
| Coating solution | % Solids | 8.3% | |

TABLE 11

PMMA VO44 3:1 dye solution

| Ingredient | Amount (g) | Wt % of total | Wt % of solids |
|---|---|---|---|
| Yamamoto SD-048 dye | 0.3 | 0.30% | 3.6% |
| MEK | 60 | 59.82% | |
| Acetone | 22 | 21.93% | |
| VO44 PMMA | 8 | 7.98% | 96.4% |
| Toluene | 10 | 9.97% | |
| Total | 100.3 | 100% | |
| Coating solution | % Solids | 8.3% | |

For each of the resulting four absorptive magenta films, the external transmission at normal incidence was measured. Representative external transmission spectra are plotted in FIG. 18 as curves 1801, 1802, 1803, and 1804. Curve 1801 corresponds to the film made from the dye solution of Table 9 (Vitel 1:2 solution), curve 1802 corresponds to the film made from the dye solution of Table 8 (Vitel 1:1 solution), curve 1803 corresponds to the film made from the dye solution of Table 10 (Vitel 3:1 solution), and curve 1804 corresponds to the film made from the dye solution of Table 11 (PMMA 3:1 solution). Pertinent optical characteristics of these absorptive magenta films (identified by their respective labels) are provided above in Table 6 from the data of FIG. 19. Also plotted in FIG. 18, as curve 1805, is the normal incidence external transmission of the multilayer optical film from FIG. 7. (The transmission spectrum 1805 and associated reflection band 1805a correspond exactly to the transmission spectrum 701 and reflection band 701a, respectively.) Such a multilayer optical film may be combined with any of the absorptive films to provide a filter for substantially enhancing the ability of individuals with CVD to distinguish or discriminate colors, with reduced glare due to the absorptive film.

The properties of the absorptive magenta films may be recalculated in terms of absorbance or optical density (OD), or in terms of absorptivity, using the techniques described above in connection with FIGS. 13-15. In this manner, the absorptivity curves 1901, 1902, 1903, 1904 of FIG. 19 were calculated based on the external transmission curves 1801, 1802, 1803, 1804, respectively. The FWHM width of the curves 1901, 1902, 1903, 1904 was calculated to be 61 nm, 81 nm, 88 nm, and 122 nm, respectively. Here again we see, like with the films made with Epolight 5391, that the width of the absorption band for these absorptive magenta films increases substantially as the dye loading increases, and as peak absorptivity increases. At the low dye loadings, this dye can provide relatively high transmission out of the reflection band wavelength range, and good absorption in band. A FWHM width of 80 nm or less may in many cases be sufficient for good glare control and acceptable out-of-band transmission.

Figure 20:
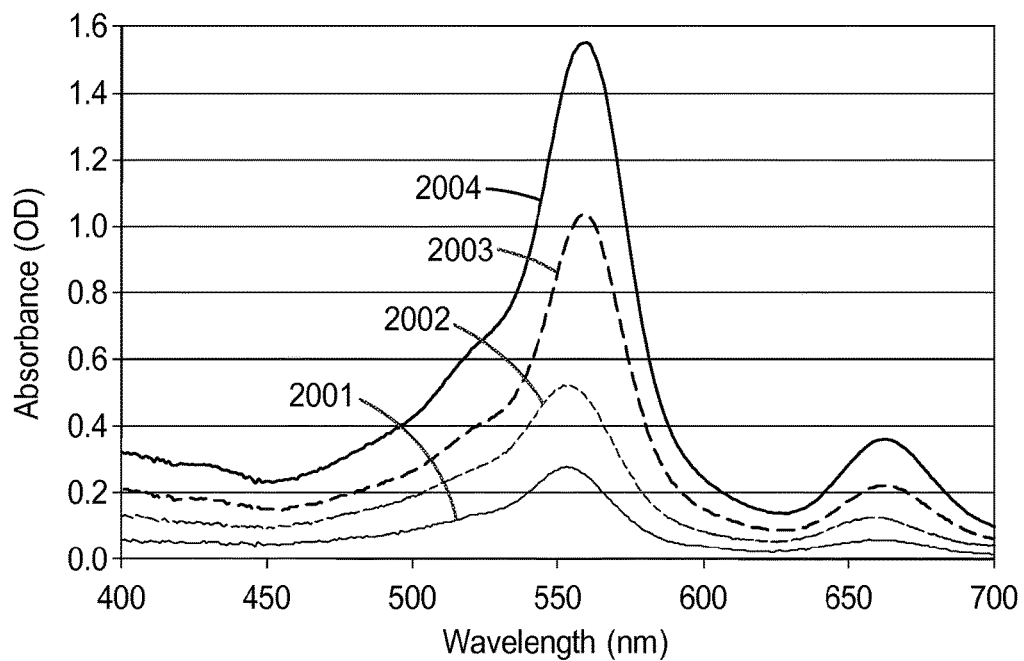
FIG. 20 is a graph of spectral absorbance (optical density) for the magenta layers in FIGS. 18 and 19.

The absorbance or optical density curves 2001, 2002, 2003, 2004 of FIG. 20 were also calculated based on the external transmission curves 1801, 1802, 1803, 1804, respectively. The FWHM width of the curves 2001, 2002, 2003, 2004 was calculated to be 47 nm, 56 nm, 40 nm, and 43 nm, respectively. This again demonstrates that the absorbance or optical density spectra of the variously dyed films have widths that are less dependent on dye loading.

Figure 21:
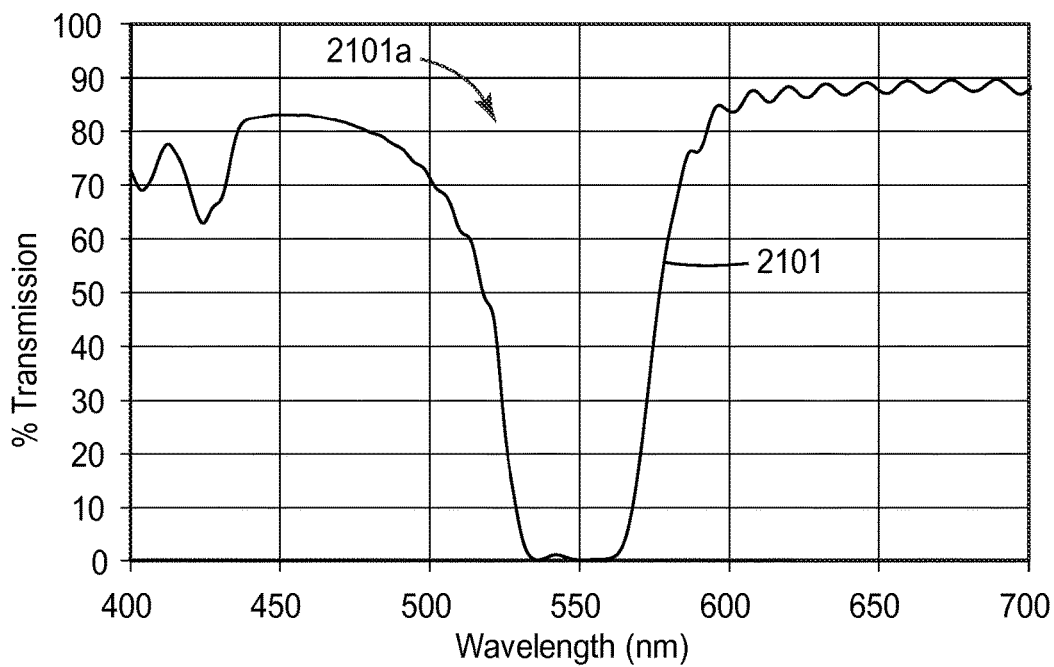
FIG. 21 is a graph of measured transmission of a filter having a narrow band green reflecting multilayer optical film in combination with an absorptive magenta layer.
Figure 22:
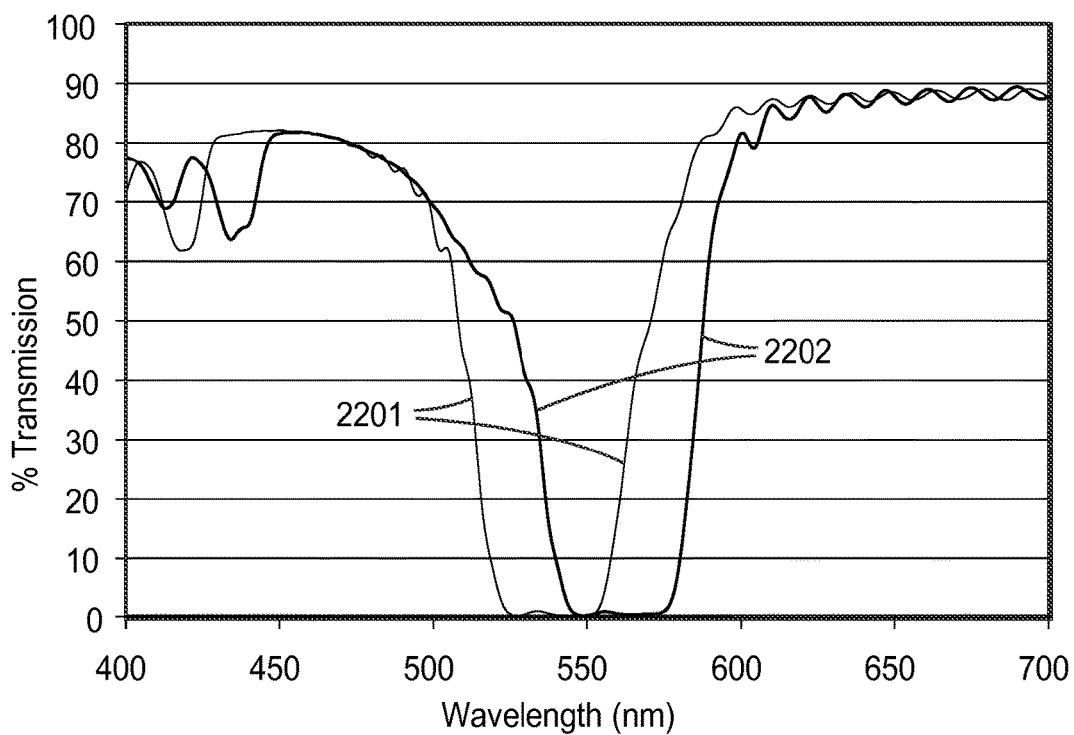
FIG. 22 is a graph of measured transmission of two filters, each of which includes a narrow band green reflecting multilayer optical film in combination with an absorptive magenta layer.
Figure 23:
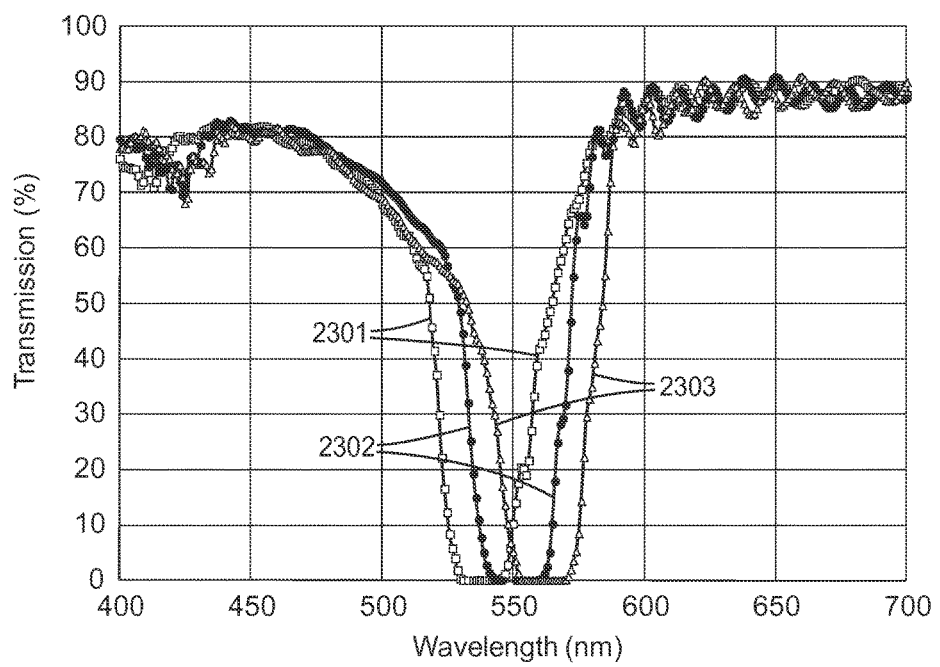
FIG. 23 is a graph of measured transmission of additional filters, each filter having a narrow band green reflecting multilayer optical film in combination with an absorptive magenta layer.

Various composite filters were made that incorporated a narrow band green reflecting multilayer optical film in combination with (laminated to) an absorptive magenta layer, and such filters were tested by CVD individual(s) for the purpose of ascertaining any improvement in color discrimination. FIGS. 21 through 23 show the measured external transmission spectra of such filters.

For the filter of FIG. 21, the narrow band green reflecting multilayer optical film of curve 701 (see FIG. 7; this film by itself had a FWHM width of 49 nm) was laminated to the absorptive magenta film of curve 1304 (see FIG. 13; this film by itself had a FWHM width of 52 nm). The resulting composite filter had a measured external transmission at normal incidence shown by curve 2101 in FIG. 21. The rejection band 2101a, disposed at or near 550 nm, can be readily seen. Pertinent optical characteristics of this composite filter are provided below in Table 12. The FWHM width of the composite filter (54 nm) is only slightly greater than that of the multilayer optical film (49 nm) or of the absorptive magenta layer (52 nm) alone.

Two composite filters are associated with FIG. 22. These filters were made in the same manner as the filter of FIG. 21, but with the casting wheel speed adjusted to shift the reflection bands to the desired wavelengths. In a first such filter, the narrow band green reflecting multilayer optical film was laminated to the absorptive magenta film of curve 1304. As in FIG. 21, the reflection band of the multilayer optical film was a third order band with a center wavelength slightly less than 550 nm, and a FWHM width of about 48 nm. The measured external transmission at normal incidence of the resulting composite filter is shown by curve 2201 in FIG. 22. Pertinent optical characteristics of this composite filter are provided below in Table 12. The FWHM is increased to 58 nm because the reflection band of the multilayer optical film moved to shorter wavelengths, but the absorption band of the dye did not. To provide a rejection band with a narrower spectral width (FWHM), it may be desirable to use an alternative dye having an absorption band at shorter wavelengths.

The second composite filter of FIG. 22 has a center wavelength of slightly more than 550 nm. The reflection band had a FWHM width of about 49 nm. This multilayer optical film was laminated to the same absorptive magenta film used in the composite filter of curve 2201. The measured external transmission at normal incidence of the resulting composite filter is shown by curve 2202. Pertinent optical characteristics of this composite filter are provided below in Table 12. The FWHM is increased to 59 nm because the reflection band of the multilayer optical film moved to shorter wavelengths, but the absorption band of the dye did not. To provide a rejection band with a narrower spectral width (FWHM), it may be desirable to use an alternative dye having an absorption band at shorter wavelengths.

Three composite filters are associated with FIG. 23, each consisting of a multilayer reflector and an absorptive magenta dye layer. The multilayer reflector for each of these three filters had 275 alternating layers of PET and coPMMA, with a layer thickness gradient that produced a first order reflection band in the infrared, the third order harmonic of which produced a visible reflection band at or near 550 nm. The precise spectral position of the visible reflection band for each of the multilayer optical films was adjusted to its desired value by changing the casting wheel speed in the extrusion process. The visible reflection band for the first multilayer optical film (a component of the first composite filter) had a center wavelength slightly less than 550 nm, the visible reflection band for the second multilayer optical film (a component of the second composite filter) had a center wavelength closest to 550 nm, and the visible reflection band for the third multilayer optical film (a component of the third composite filter) had a center wavelength slightly greater than 550 nm. To produce the composite filters, each of these multilayer optical films was attached to an absorptive magenta film. In each case, the absorptive magenta film used was the absorptive magenta dye film with the dye loading indicated by curve 2501 (see FIG. 25 below), which has an internal transmission minimum of 51%. This is also the same dyed film used and measured for curve 1602. Curve 1703 shows the external transmission of this same dye layer. The combination of this absorptive magenta film with the three multilayer optical films produced the first, second, and third composite filters whose measured external transmission at normal incidence are shown by curves 2301, 2302, and 2303 respectively in FIG. 23. The rejection bands of these filters, which are a combination of the ($3^{rd}$ order) reflection band of the respective multilayer optical film and the absorption band of the absorptive magenta film, can be clearly seen in the figure. Pertinent optical characteristics of these composite filters are provided below in Table 12. Note that the narrow spectral width (FWHM) values of curves 2301 to 2303 are only slightly larger than the base optical film values of 35 nm (curve 1701) after the addition of the magenta layer of curve 1602 (68 nm FWHM).

TABLE 12 optical properties of multilayer optical film + absorptive film combinations

| Film (curve label) | λ1 (nm) | λ2 (nm) | FWHM bandwidth (nm) | λ center (nm) | int T % avg 10 nm range incl. 550 nm | int T % avg 420 to 680 | int T % avg 420 to λ1, λ2 to 680 |
|---|---|---|---|---|---|---|---|
| 2101 | 521 | 575 | 54 | 548 | 0.44 (545-555) | 73.1 | 89.5 |
| 2201 | 509 | 567 | 58 | 538 | 0.34 (540-550) | 73.0 | 90.3 |
| 2202 | 528 | 587 | 59 | 557 | 0.57 (545-555) | 70.3 | 87.4 |
| 2301 | 519 | 562 | 43 | 540 | 2.12 (540-550) | 77.3 | 89.5 |
| 2302 | 531 | 572 | 41 | 551 | 0.01 (545-555) | 77.3 | 89.5 |
| 2303 | 535 | 582 | 47 | 558 | 1.05 (550-560) | 74.6 | 87.4 |

Figure 24A:
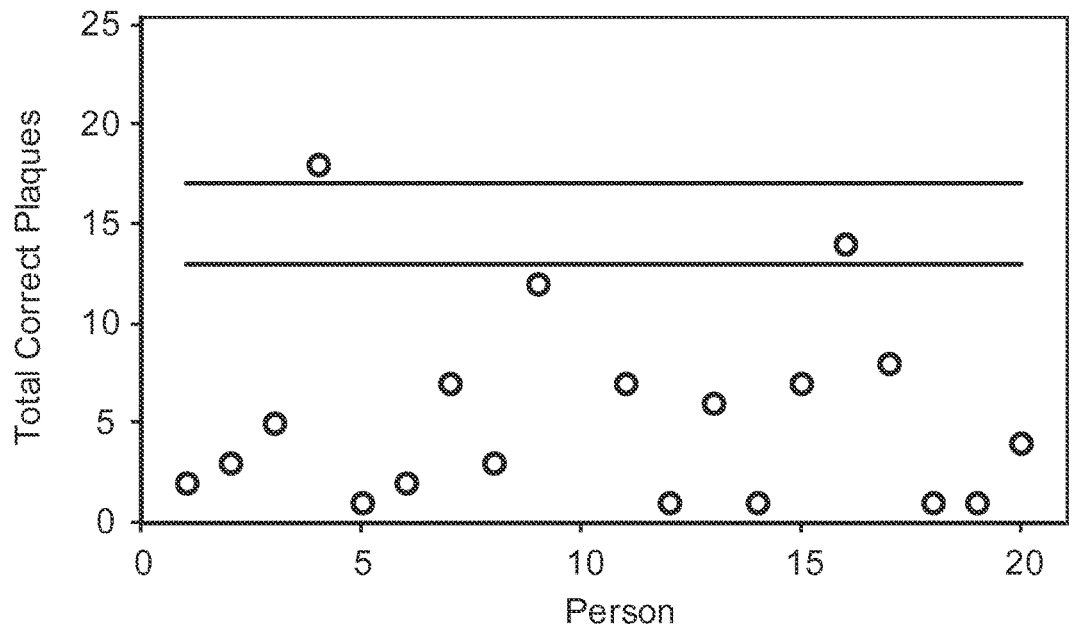
FIG. 24A is a graph showing the number of Ishihara plaques correctly assessed (out of a total of 25 plaques) by 19 different individuals, most of whom were CVD, without filtering.
Figure 24B:
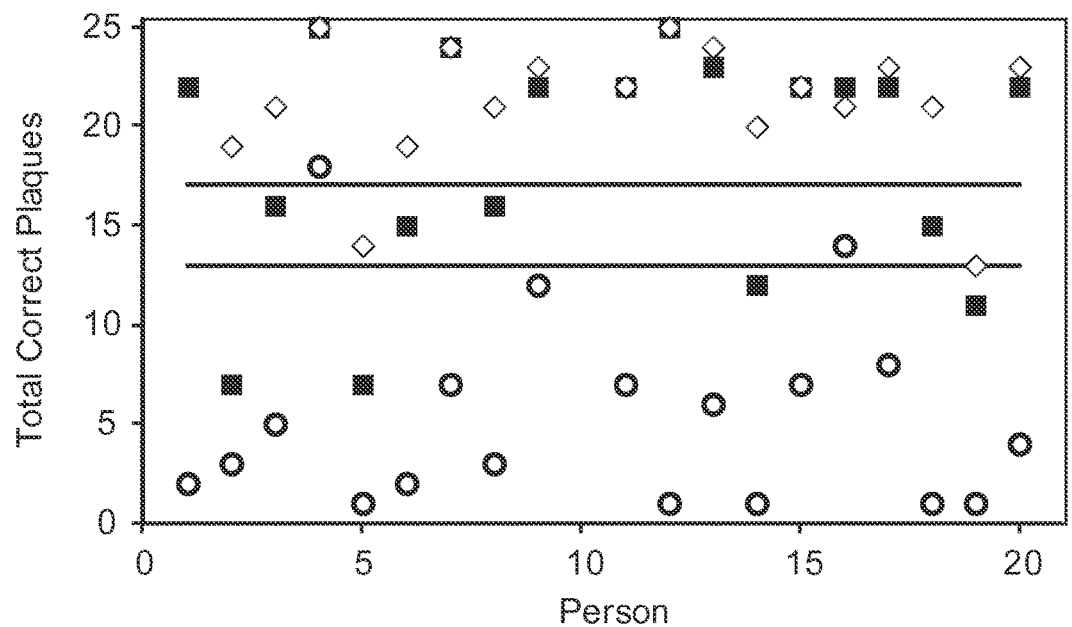
FIG. 24B is a graph similar to that of FIG. 24A but where the 19 individuals each observed the Ishihara plaques through a specific narrow band filter.

The composite filter of FIG. 21 was tested by 19 individuals, most of whom were CVD. (One individual was known to have normal color vision and was not CVD (see person #10 in FIGS. 24A, 24B); another individual believed himself to be CVD but the testing revealed he was not (see person #4 in FIGS. 24A, 24B); still another individual, who did have CVD, was tested two times, and the results are reported separately as two persons, namely, person #1 and person #11.) The filter was inserted into eyeglass frames which held the film with a cylindrical radius of curvature of about 60 mm and with the center of curvature of each lens positioned directly behind the retina of each eye for viewing at normal incidence to the film surface. Each individual attempted to read the numeric pattern in 25 Ishihara test plates without using the filtered eyeglasses and in an environment of a windowed room with a balanced mix of diffuse sunlight and fluorescent ceiling lights. The resulting number of Ishihara test plates that were correctly identified (out of the total of 25) by each individual is plotted in FIG. 24A. (A data point is not plotted for person #10, which is the individual known to have normal color vision. This person recognized all 25 Ishihara test plates.) In this graph, the vertical axis is the number of Ishihara test plates correctly identified, and the horizontal axis is the identification number (from 1 to 20) of the individual who undertook the test (with the caveat that two of the "persons" on the horizontal axis is one person who was tested twice). By standardized methodology, a score of 13 or fewer correct responses indicates deficient color vision, and a score of 17 or more correct responses indicates normal color vision. Thin horizontal lines are provided on the graph at 13 and 17 for reference purposes. It is apparent that almost all of the 20 individuals had deficient color vision.

Each of the same 19 individuals then re-took the test while wearing the filtered eyeglasses, but otherwise under substantially the same conditions. The results for all 19 individuals are plotted as square-shaped data points in the graph of FIG. 24B, which is set up in the same way as that of FIG. 24A. The original data points (wherein the individuals did not wear the filtered eyeglasses) are also reproduced for convenience in FIG. 24B, the original data points being drawn as circular-shaped data points. Note again that two of the "persons" on the horizontal axis of FIG. 24B, person #1 and person #11, is one CVD individual who was tested twice. Also, person #10 recognized all 25 Nishihara plates once again in this test with the filtered eyeglasses.

Each of the same 19 individuals, except person #1, also re-took the test while wearing the filtered eyeglasses, but under different illumination conditions: the room was illuminated only with overhead fluorescent lights. Person #1 was called back to re-test as person #11 so that he too would be subject to this part of the test. The results in this case for all 19 individuals are plotted as diamond-shaped data points in the graph of FIG. 24B (keeping in mind that person #10, for whom no data point is provided, once again recognized all 25 Ishihara test plates).

Color discrimination tests were also performed with the filters of FIG. 22. For these tests, the filtered glasses were modified so that the filter of FIG. 21 was replaced with the filter of curve 2201 (whose center wavelength is shown as 538 nm in Table 12 above), and having the same cylindrical configuration, which provides approximately normal incidence viewing from the perspective of the viewer's eyes. Generally speaking, the CVD individuals within the group noticed that both the eyeglasses with the filter of curve 2101, and the eyeglasses with the filter of curve 2201, provided significantly improved color discrimination when compared to viewing Ishihara test plates with no filtered eyeglasses.

Generally, the degree of improvement was about the same for these two types of eyeglasses, and most CVD individuals could not discern any difference between the filters of curves 2101 and 2201.

Color discrimination tests were also performed with the filters of FIG. 23, and several other filters. In these tests, one of the 19 individuals discussed above in connection with FIG. 21, who was CVD and who was deemed to be fairly representative of the CVD individuals within the group of 19, was presented with several different Ishihara test plates and was asked to read the numeric pattern in each plate. Illumination conditions were controlled. The individual's successes and failures in reading the Ishihara test plate numbers were recorded, when using "no filter" and when using eyewear to which was applied one of the following filters:

the composite filter of curve 2301 (FIG. 23);
the composite filter of curve 2302 (FIG. 23);
the composite filter of curve 2303 (FIG. 23);
the composite filter of curve 2101 (FIG. 21);
a filter that consisted of only a piece of multilayer optical film (referred to herein as MB530) having the following internal transmission characteristics at normal incidence: $\lambda 1=513$ nm; $\lambda 2=548$ nm; FWHM bandwidth=35 nm; $\lambda$ center=530 nm; int T % avg over a 10 nm wide wavelength range that includes 550 nm=38% (over the range from 540-550 nm, which range was selected to provide the smallest numerical result); int T % avg from 420 to 680 nm=86%; int T % avg from 420 to $\lambda 1$ and $\lambda 2$ to 680 nm=97%; and
a filter that consisted of only a piece of multilayer optical film (referred to herein as MB570) having the following characteristics at normal incidence: $\lambda 1=552$ nm; $\lambda 2=588$ nm; FWHM bandwidth=36 nm; 2 center=570 nm; int T % avg over a 10 nm wide wavelength range that includes 550 nm=31% (over the range from 550-560 nm, which range was selected to provide the smallest numerical result); int T % avg from 420 to 680 nm=85%; int T % avg from 420 to $\lambda 1$ and $\lambda 2$ to 680 nm=96%.

Table 13 contains the CVD individual's observations/interpretations of the Ishihara numeric patterns in an environment of a windowed room with all electric lights turned off and daylight entering the room through the windows, for each of the above filtering conditions. The capability of a given filter to improve the individual's color discrimination can be ascertained by comparing, for each of the tested Ishihara plates, (1) the actual numeric pattern; (2) the CVD individual's interpretation of the numeric pattern when using no filter; and (3) the CVD individual's interpretation of the numeric pattern when using the given filter.

TABLE 13

| | | | | | | | | |
|---|---|---|---|---|---|---|---|---|
| CVD individual's numeric pattern interpretations (daylight only) | | | | | | | | |
| Ishihara plate | Actual numeric pattern | Filter: none | Filter: MB530 | Filter: curve 2301 | Filter: curve 2302 | Filter: curve 2101 | Filter: curve 2303 | Filter: MB570 |
| 2 | 8 | faint 3 | faint 3 | 3 | 3 | 3 | 3 | faint 3 |
| 8 | 15 | 17 | 17 | faint 15 | 15 | 15 | faint 15 | 17 |
| 9 | 74 | 71 or 21 | 71 or 21 | 71 or74 | 71 or 74 | 74 | 71 | 71 or 21 |
| 13 | 45 | nothing | nothing | nothing | faint 45 | faint 45 | nothing | nothing |
| 16 | 16 | nothing | nothing | faint 16 | faint 16 | 16 | faint 16 | nothing |

Table 14 contains the same CVD individual's observations/interpretations of the same Ishihara numeric patterns and with the same filtering conditions as Table 13, but in an environment of a room that was brightly lit only with overhead fluorescent lights:

TABLE 14

CVD individual's numeric pattern interpretations (fluorescent lighting only)

| Ishihara plate | Actual numeric pattern | Filter: none | Filter: MB530 | Filter: curve 2301 | Filter: curve 2302 | Filter: curve 2101 | Filter: curve 2303 | Filter: MB570 |
|---|---|---|---|---|---|---|---|---|
| 2 | 8 | faint 3 | faint 8 | 8 | bold 8 | bold 8 | 8 | nothing |
| 8 | 15 | 17 | faint 15 | 15 | 15 | 15 | 15 | 17 |
| 9 | 74 | 21 or 71 | 71 | 74 | 74 | bold 74 | 74 | 21 or 71 |
| 13 | 45 | nothing | nothing | faint 45 | faint 45 | faint 45 | faint 45 | nothing |
| 16 | 16 | nothing | nothing | 16 | 16 | bold 16 | 16 | nothing |

In addition to and/or instead of absorptive magenta films, which selectively absorb visible green wavelengths, the disclosed filters may also include other colored absorptive films or layers. For example, a layer that selectively absorbs blue and red visible wavelengths, or a layer that selectively absorbs blue visible wavelengths, can be used to at least partially balance the transmissive color of the filter, towards a more neutral white (or gray). If no attempt is made to color balance, the filter will typically have a strong or at least significant magenta appearance in transmission due to the strong blocking over a portion of the green wavelength range. Such an appearance may be deemed objectionable by some users, even if those users find the filter to be helpful in enhancing color discrimination. On the other hand, excessive color balancing may counteract the ability of the filter to enhance color discrimination. For example, if color discrimination is enhanced by a multilayer optical film that selectively blocks a portion of green light and freely passes blue light, red light, and remaining green light, then an absorptive filter that blocks red and blue light but passes green light may well counteract partially or completely the effect of the multilayer optical film.

We have found that some color balancing in the disclosed filters is often desirable, and can be compatible with the enhancement of color discrimination, including red/green color discrimination.

Figure 25:
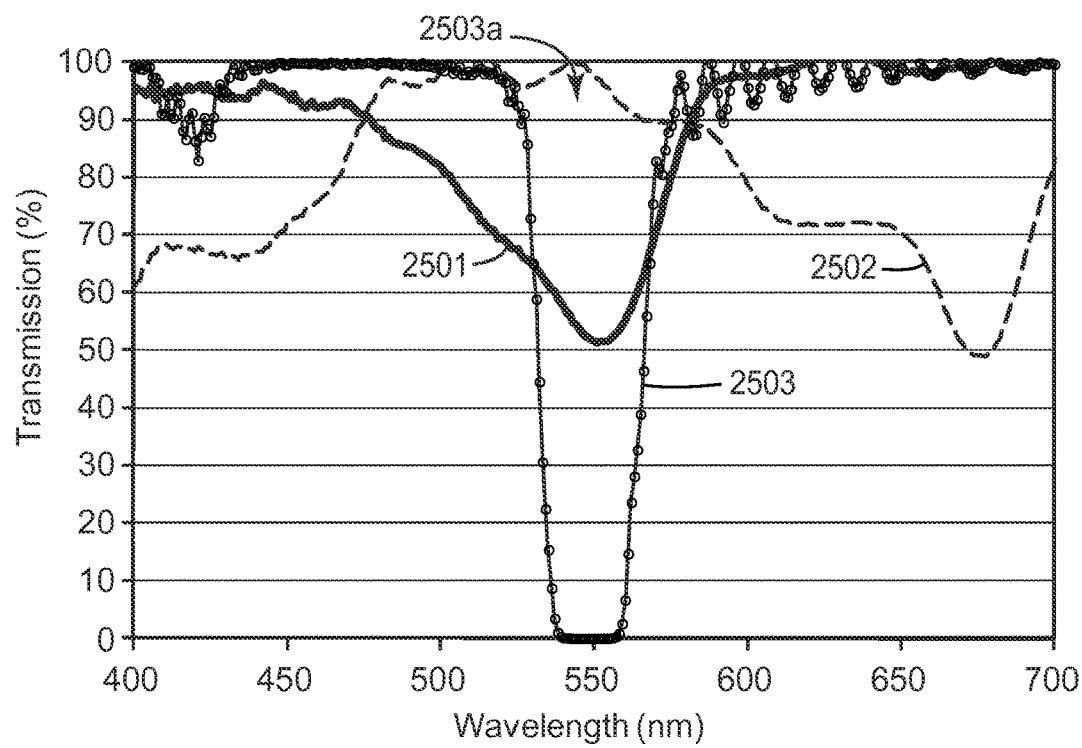
FIG. 25 is a graph of internal transmission of a narrow band green reflecting multilayer optical film, an absorptive magenta layer, and a layer that selectively absorbs blue and red wavelengths.

A film coated with a green dye (type 213 White flame Green) was obtained from LEE Filters (www.leefilters.com). A "green" dye in this regard refers to a dye that selectively absorbs blue and red wavelengths and transmits green light, thus having a green appearance in transmission. The internal transmission spectrum of this absorptive green film is plotted as curve 2502 in FIG. 25. Also plotted in FIG. 25 is the internal transmission spectrum (see curve 2501) of a magenta dye, in particular, a magenta dye made using the Epolight 5391 dye. Finally, curve 2503 plots the internal transmission of a narrow band green reflecting multilayer optical film. This multilayer optical film is the same film associated with curves 1601 and 1701 in FIGS. 16 and 17 respectively. The reflection band of the film can be seen at 2503a. A mathematical procedure similar to the one described above was used to remove the effects of outer polymer/air surface reflections from external transmission measurements so as to obtain the internal transmission curves 2501, 2502, 2503.

Figure 26:
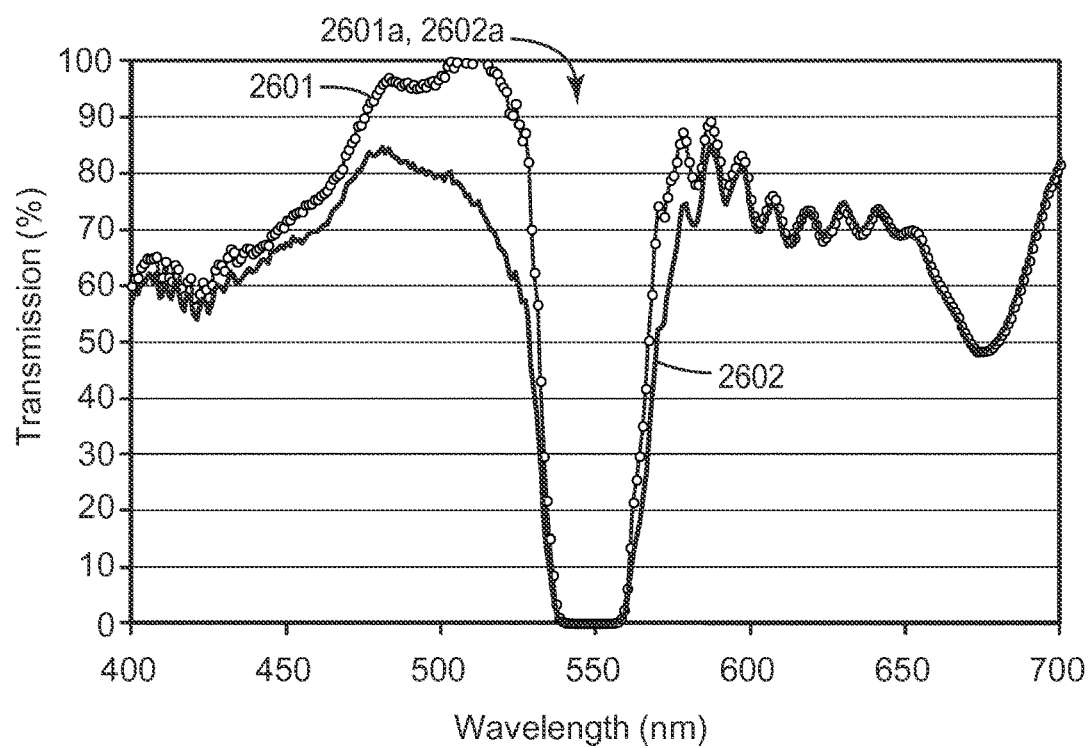
FIG. 26 is a graph of internal transmission of a first filter consisting of a narrow band green reflecting multilayer optical film in combination with a layer that selectively absorbs blue and red wavelengths, and a second filter in which an absorptive magenta layer is added to the first filter.

The internal transmission curves in FIG. 25 can be used to mathematically construct or simulate one or more composite filter. A first composite filter of interest is a laminate of all three films of FIG. 25: the multilayer optical film (curve 2503), the absorptive magenta film (curve 2501), and the absorptive green film (curve 2502). If the three films are laminated together with optically clear adhesives, the internal transmission of the resulting first composite filter would be combination of curves 2501, 2502, and 2503. Such a combination, i.e., the internal transmission of the first composite filter, is shown as curve 2602 in FIG. 26. A second composite filter of interest is a laminate of the multilayer optical film (curve 2503) and the absorptive green film (curve 2502). If these two films are laminated together with an optically clear adhesive, the internal transmission of the resulting second composite filter would be curve 2601 in FIG. 26. Note that the difference between the simulated first composite filter (curve 2602) and the simulated second composite filter (curve 2601) is the absence of the absorptive magenta film in the second composite filter.

Using straightforward computational procedures, we can also investigate the effect of heavier or lighter dye loading for the absorptive green film in each of the simulated composite filters. One reason for doing this may be to see how such changes in the amount of green dye can change the apparent color of the composite filter, e.g. for purposes of at least partial color balancing. For simplicity, we may associate the curve 2502 in FIG. 25 with a green dye loading value of 1, or "1×". With this baseline, it is a straightforward matter to compute the internal transmission (or absorptivity, etc.) the absorptive green film would have with twice the original dye loading (2×), or three times the original dye loading (3×), or even zero dye loading (0×, i.e., with the absorptive green film omitted from the filter).

With these simulation tools, the simulated first composite filter (see curve 2602, for the case of 1×green dye loading plus magenta dye) can be shown to have the following optical properties as a function of green dye loading:

TABLE 15 optical properties of simulated first composite filter

| green dye loading | 0X | 0.5X | 1X | 1.5X | 2X | 2.5X | 3X |
|---|---|---|---|---|---|---|---|
| Chromaticity x | 0.3238 | 0.3203 | 0.3164 | 0.3121 | 0.3074 | 0.3024 | 0.2970 |
| Chromaticity y | 0.2431 | 0.2542 | 0.2656 | 0.2773 | 0.2892 | 0.3012 | 0.3133 |
| T lum | 55.20 | 51.21 | 47.71 | 44.63 | 41.89 | 39.47 | 37.30 |

TABLE 15-continued optical properties of simulated first composite filter

| green dye loading | 0X | 0.5X | 1X | 1.5X | 2X | 2.5X | 3X |
|---|---|---|---|---|---|---|---|
| T a* | 48.82 | 39.41 | 30.52 | 22.13 | 14.21 | 6.73 | −0.33 |
| T b* | −29.27 | −24.67 | −20.42 | −16.49 | −12.88 | −9.56 | −6.53 |
| T L* | 79.15 | 76.81 | 74.64 | 72.64 | 70.80 | 69.09 | 67.50 |

The simulated second composite filter (see curve 2601, for the case of 1×green dye loading and no magenta dye) can be similarly shown to have the following optical properties as a function of green dye loading:

TABLE 16 optical properties of simulated second composite filter

| green dye loading | 0X | 0.5X | 1X | 1.5X | 2X | 2.5X | 3X |
|---|---|---|---|---|---|---|---|
| Chromaticity x | 0.3134 | 0.3095 | 0.3052 | 0.3006 | 0.2956 | 0.2902 | 0.28 |
| Chromaticity y | 0.2607 | 0.2732 | 0.2860 | 0.2989 | 0.3120 | 0.3251 | 0.34 |
| T lum | 65.40 | 61.13 | 57.37 | 54.03 | 51.06 | 48.41 | 46.04 |
| T a* | 35.34 | 25.57 | 16.38 | 7.71 | −0.45 | −8.13 | −15.37 |
| T b* | −25.12 | −20.27 | −15.79 | −11.66 | −7.88 | −4.42 | −1.26 |
| T L* | 84.69 | 82.45 | 80.39 | 78.48 | 76.72 | 75.08 | 73.57 |

These Tables 15 and 16 assume the following: illuminant CIE D65; observer 10 degree–1964; wavelength interval 1 nm. Furthermore, in these tables, "chromaticity x" and "chromaticity y" refer to the color coordinates of the simulated composite filter in terms of the CIE 1931 x,y chromaticity diagram; "T lum" refers to the luminous transmission as defined in that color system, "T a*" and "T b*" and "T L*" refer to the color and transmission parameters as defined in the CIE 1976 L*a*b* color space or CIELAB.

Figure 27:
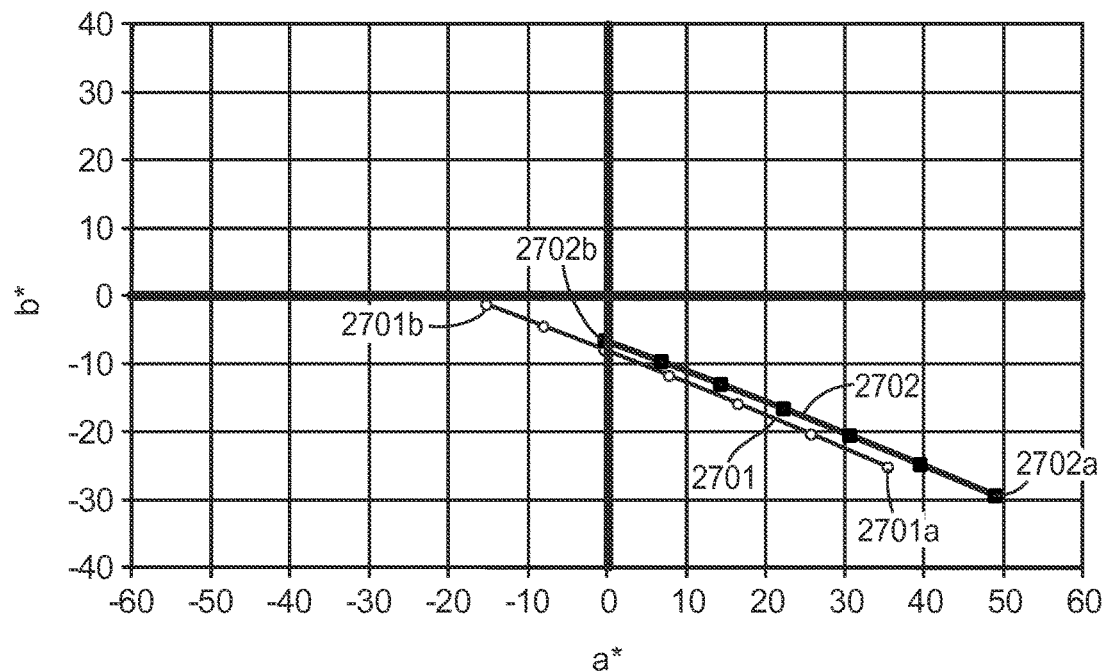
FIG. 27 is a graph showing calculated color coordinates (a*, b*) for filters similar to those of FIG. 26, but where the red/blue absorptive layer is varied from heavy dye loading to light dye loading.

The (a*, b*) color coordinates of the simulated first and second composite filters are plotted in FIG. 27 as a function of green dye loading in the absorptive green layer. Curve 2702 plots the (a*, b*) color coordinates of the simulated first composite filter. The end 2702a of the curve corresponds to zero green dye loading (0×), and the end 2702b corresponds to a green dye loading of 3×. Curve 2701 plots the (a*, b*) color coordinates of the simulated second composite filter. The end 2701a of the curve corresponds to zero green dye loading (0×), and the end 2701b corresponds to a green dye loading of 3×. From these curves one can see that regardless of whether the filter includes an absorptive magenta layer or film, an absorptive green film with even a small green dye loading can help to adjust the color of the filter closer to the neutral color point (0, 0), by at least some amount. The color balancing is facilitated by the use of a narrow band green blocking film or filter that blocks only a portion of the wavelengths of green light. If the green blocking reflector or dye exhibited a much wider band width (FWHM), such as equal to or greater than 80 nm or 100 nm, a color balance would be difficult or impossible.

Figure 28:
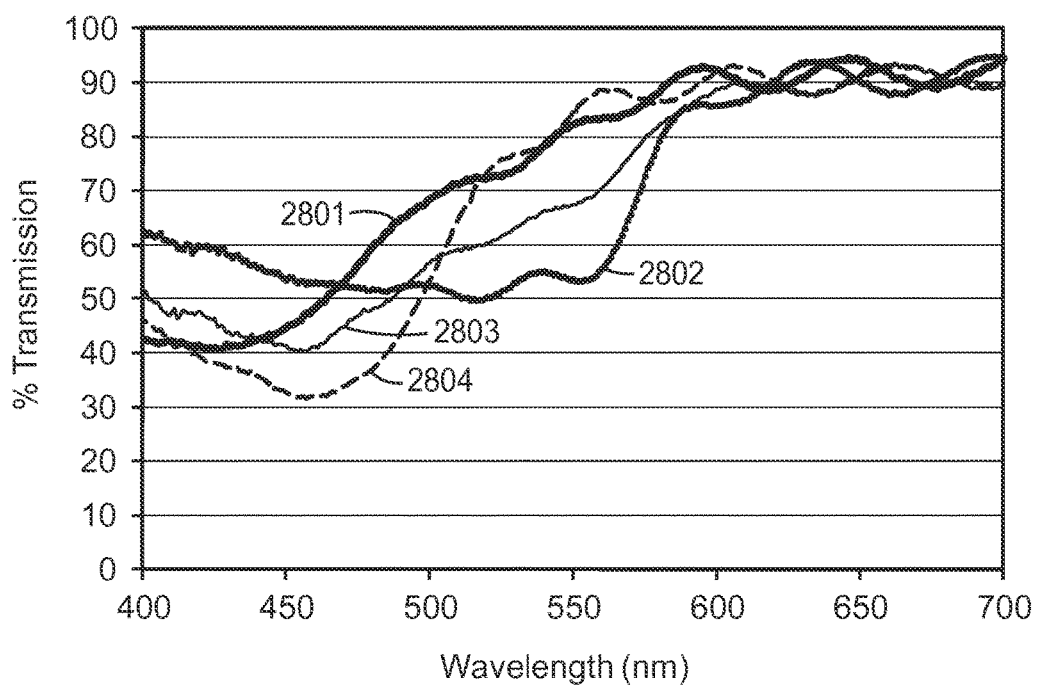
FIG. 28 is a graph of measured transmission of various blue-absorbing dye layers that were incorporated into some narrow band green blocking filters.

We also investigated the effect of some colored absorptive films other than colored magenta films on the capability of a given filter to assist a CVD individual with color discrimination. Four different colored absorptive films were made using dyes obtained from LEE Filters (www.leefilters.com). At least three of the dyes absorbed more strongly at blue wavelengths than at green or red wavelengths. A first absorptive film was made with Lee dye type 764; the measured external transmission of the film is shown as curve 2801 in FIG. 28. A second absorptive film was made with Lee dye type 151; the measured external transmission of the film is shown as curve 2802 in FIG. 28. A third absorptive film was made with Lee dye type 009; the measured external transmission of the film is shown as curve 2803 in FIG. 28. A fourth absorptive film was made with Lee dye type 765; the measured external transmission of the film is shown as curve 2804 in FIG. 28.

The same CVD individual tested in connection with Tables 13 and 14 above was tested in a similar fashion, with four of the Ishihara plates. Testing was done in an environment of a windowed room with all electric lights turned off and bright daylight entering the room through the windows. The individual was asked to identify the numeric pattern when viewing the Ishihara plate through the multilayer optical film of curve 2302 (see FIG. 23 above), and through the same multilayer optical film in combination with each of the four colored absorptive films of FIG. 28. The CVD individual's interpretations of the numeric pattern under the various conditions are summarized below in Table 17. The effect of the various colored absorptive films on the color discrimination function of the multilayer optical film can be ascertained by comparing, for each of the tested Ishihara plates, (1) the actual numeric pattern; (2) the CVD individual's interpretation of the numeric pattern when using only the multilayer optical film of curve 2302; and (3) the CVD individual's interpretation of the numeric pattern when using the multilayer optical film in combination with the given colored absorptive film.

TABLE 17 effect of other colored absorptive films on a CVD individual's
numeric pattern interpretations (bright day, indirect sunlight only)

| Ishihara plate | actual numeric pattern | Filter: curve 2302 | Filter: curves 2302, 2801 | Filter: curves 2302, 2802 | Filter: curves 2302, 2803 | Filter: curves 2302, 2804 |
|---|---|---|---|---|---|---|
| 2 | 8 | 3 | no improvement | Clearer 3 or 8 | Clearer 3 or 8 | no improvement |
| 8 | 15 | 15 | slightly clearer 15 | clearer 15 | clearer 15 | no improvement |
| 13 | 45 | faint 45 | slightly clearer 45 | clearer 45 | slightly clearer 45 | less clear |
| 16 | 16 | faint 16 | slightly clearer 16 | much clearer 16 | clearer 16 | no improvement |

Unless otherwise indicated, all numbers expressing quantities, measurement of properties, and so forth used in the specification and claims are to be understood as being modified by the term "about". Accordingly, unless indicated to the contrary, the numerical parameters set forth in the specification and claims are approximations that can vary depending on the desired properties sought to be obtained by those skilled in the art utilizing the teachings of the present application. Not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, to the extent any numerical values are set forth in specific examples described herein, they are reported as precisely as reasonably possible. Any numerical value, however, may well contain errors associated with testing or measurement limitations.

Various modifications and alterations of this invention will be apparent to those skilled in the art without departing from the spirit and scope of this invention, and it should be understood that this invention is not limited to the illustrative embodiments set forth herein. The reader should assume that features of one disclosed embodiment can also be applied to all other disclosed embodiments unless otherwise indicated. It should also be understood that all U.S. patents, patent application publications, and other patent and non-patent documents referred to herein are incorporated by reference, to the extent they do not contradict the foregoing disclosure.

The invention claimed is:

1. A filter suitable for use in improving color discrimination for individuals with color vision deficiency, comprising:
a multilayer optical film having, an angle of incidence, an average internal transmission from 420-680 nm of at least 50%, the film also having at the angle of incidence a reduced transmission band defined by an average internal transmission of 10% or less over a 10 nm wide wavelength range that includes 550 nm, the reduced transmission band being found in a reflection band of the film having a full width at half maximum value of 60 nm or less; and
an absorptive magenta layer disposed on one side of the multilayer optical film, the absorptive magenta layer selectively absorbing green light.

2. The filter of claim 1, wherein the film has at the angle of incidence an average internal transmission of 5% or less over the 10 nm wide wavelength range.

3. The filter of claim 2, wherein the film has at the angle of incidence an average internal transmission of 2% or less, or 1% or less over the 10 nm wide wavelength range.

4. The filter of claim 1, wherein the film has at the angle of incidence an internal transmission at 550 nm of 10% or less.

5. The filter of claim 4, wherein the film has at the angle of incidence an internal transmission at 550 nm of 5% or less, or 2% or less, or 1% or less.

6. The filter of claim 1, wherein the filter has at the angle of incidence an average internal transmission from 420-680 nm of at least 60%.

7. The filter of claim 6, wherein the filter has at the angle of incidence an average internal transmission from 420-680 nm of at least 70%.

8. The filter of claim 1, wherein the full width at half maximum of the reflection band is 50 nm or less.

9. The filter of claim 8, wherein the full width at half maximum of the reflection band is in a range from 20 to 50 nm.

10. The filter of claim 9, wherein the full width at half maximum of the reflection band is in a range from 20 to 40 nm.

11. The filter of claim 1, wherein the full width at half maximum of the reflection band defines a short wavelength band edge and a long wavelength band edge of the reflection band, and wherein the multilayer optical film has an internal transmission, when averaged from 420 nm to the short wavelength band edge and from the long wavelength band edge to 680 nm, of at least 60%, at the angle of incidence.

12. The filter of claim 11, wherein the internal transmission of the multilayer optical film, when averaged from 420 nm to the short wavelength band edge and from the long wavelength band edge to 680 nm, is at least 75%, or at least 90%.

13. The filter of claim 1, wherein the reflection band is a harmonic of an infrared reflection band.

14. Eyewear comprising a filter suitable for use in improving color discrimination for individuals with color vision deficiency, the filter including a multilayer optical film in combination with an absorptive layer, the multilayer optical film having, at an angle of incidence, an average internal transmission from 420-680 nm of at least 50%, the film also having at the angle of incidence a reduced transmission band defined by an average internal transmission of 10% or less over a 10 nm wide wavelength range that includes 550 nm, the reduced transmission band being found in a reflection band of the film having full width at half maximum of 60 nm or less.

15. The eyewear of claim 14, wherein the filter has a radius of curvature greater than 100 mm.

16. The eyewear of claim 14, wherein the filter consists essentially of the multilayer optical film.

17. The eyewear of claim 14, wherein the absorptive layer is disposed on a side of the filter which faces a user of the eyewear.

18. The eyewear of claim 14, wherein the absorptive layer selectively absorbs green light.

19. A filter, comprising:
   a multilayer optical film having a visible reflection band; and
   an absorptive magenta layer disposed on one side of the multilayer optical film, the absorptive magenta layer having an absorption band that selectively absorbs green light;
   wherein the visible reflection band at an angle of incidence in combination with the absorption band provide a rejection band of the filter, the rejection band having a full width at half maximum of 60 nm or less;
   wherein a combination of the multilayer optical film and the absorptive magenta layer have a reduced transmission band defined by an average internal transmission of 10% or less at the angle of incidence over a 10 nm wide wavelength range that includes 550 nm, the reduced transmission band being found in the rejection band; and
   wherein the combination of the multilayer optical film and the absorptive magenta layer have a maximum percent reflectivity over a wavelength range from 500 to 600 nm of less than 50%, for light incident on the combination at the angle of incidence and from a direction such that the light passes through the absorptive magenta layer before being incident on the multilayer optical film.

* * * * *

UNITED STATES PATENT AND TRADEMARK OFFICE
CERTIFICATE OF CORRECTION

PATENT NO. : 10,054,803 B2
APPLICATION NO. : 14/759244
DATED : August 21, 2018
INVENTOR(S) : Wold et al.

Page 1 of 1

It is certified that error appears in the above-identified patent and that said Letters Patent is hereby corrected as shown below:

In the Claims

Column 37, Line 53, in Claim 1, delete "an" and insert -- at an --, therefor.

Signed and Sealed this
Second Day of October, 2018

Andrei Iancu
*Director of the United States Patent and Trademark Office*